United States Patent
Kim et al.

(10) Patent No.: US 11,213,201 B2
(45) Date of Patent: Jan. 4, 2022

(54) VISION CORRECTION SURGERY RECOMMENDATION METHOD AND DEVICE

(71) Applicant: VISUWORKS, Seoul (KR)

(72) Inventors: Jin Kuk Kim, Seoul (KR); Ik Hee Ryu, Seoul (KR)

(73) Assignee: VISUWORKS, Seoul (KR)

( * ) Notice: Subject to any disclaimer, the term of this patent is extended or adjusted under 35 U.S.C. 154(b) by 0 days.

(21) Appl. No.: 17/084,510

(22) Filed: Oct. 29, 2020

(65) Prior Publication Data

US 2021/0059521 A1 Mar. 4, 2021

Related U.S. Application Data

(63) Continuation of application No. PCT/KR2019/010959, filed on Aug. 27, 2019.

(51) Int. Cl.

| | |
|---|---|
| *A61B 3/107* | (2006.01) |
| *A61B 5/00* | (2006.01) |
| *A61F 9/008* | (2006.01) |
| *G06N 20/00* | (2019.01) |
| *G16H 20/40* | (2018.01) |
| *G16H 50/30* | (2018.01) |

(52) U.S. Cl.
CPC ............ *A61B 3/107* (2013.01); *A61B 5/7275* (2013.01); *A61F 9/008* (2013.01); *G06N 20/00* (2019.01); *G16H 20/40* (2018.01); *G16H 50/30* (2018.01); *A61F 2009/00872* (2013.01)

(58) Field of Classification Search
CPC .................................................... A61B 34/10
See application file for complete search history.

(56) References Cited

U.S. PATENT DOCUMENTS

| | | |
|---|---|---|
| 2004/0054358 A1 | 3/2004 | Cox et al. |
| 2007/0161972 A1 | 7/2007 | Felberg |

(Continued)

FOREIGN PATENT DOCUMENTS

| | | |
|---|---|---|
| JP | 2005-521473 A | 7/2005 |
| KR | 10-2012-0110176 A | 10/2012 |
| KR | 10-2016-0030389 A | 3/2016 |

OTHER PUBLICATIONS

International Search Report and Written Opinion dated May 26, 2020 as received in application No. PCTKR2019/010959.

*Primary Examiner* — Scott Luan
(74) *Attorney, Agent, or Firm* — Maschoff Brennan

(57) ABSTRACT

The present invention relates to a method for recommending a vision correction surgery, and the method according to one aspect of the present invention comprises: obtaining an examination data of a subject; predicting whether the vision correction surgery is suitable for the subject from the examination data; when the vision correction surgery is suitable for the subject, predicting whether the vision correction surgery using a laser is available for the subject from the examination data; when the vision correction surgery using the laser is available for the subject, calculating corneal shape factor prediction values of the subject after a standard vision correction surgery and a custom vision correction surgery from the examination data; and when the vision correction surgery using the laser is available for the subject, suggesting a vision correction surgery corresponding to the subject from the examination data.

11 Claims, 44 Drawing Sheets

(56) References Cited

U.S. PATENT DOCUMENTS

2014/0081396 A1    3/2014  Maillard
2018/0000342 A1*  1/2018  Tang .................... G06T 7/0014
2018/0161098 A1*  6/2018  Gupta .................... A61B 34/10

* cited by examiner

VISION CORRECTION SURGERY RECOMMENDATION METHOD AND DEVICE

TECHNICAL FIELD

The present disclosure relates to a method and device for recommending a vision correction surgery, and specifically, to a method and device for recommending a vision correction surgery to a subject or the like using artificial intelligence.

BACKGROUND ART

Vision correction surgeries such as laser-assisted in situ keratomileusis (LASIK) and laser-assisted sub-epithelial keratectomy (LASEK) have gained a great deal of attention from people with poor vision regardless of age or gender. The interest in vision correction surgeries is increasing day by day to the extent that there are statistics that the number of people who have undergone the vision correction surgeries has reached 100,000.

However, it is difficult for a subject who wants to undergo a vision correction surgery to determine which vision correction surgery is suitable for himself or herself. The subject should basically select a type of surgery such as LASIK, LASEK, small incision lenticule extraction (SMILE), or lens implantation. In addition, the subject should select a type of surgery according to surgical equipment, such as iLASIK, DaVinci LASIK, crystal LASIK, Z-LASIK, VISU LASIK, OPTI LASIK, or the like, or according to a surgical method, such as Contoura vision, extra LASIK, wavefront LASIK, or the like. Further, since the recommended corneal cutting amount varies depending on hospitals and doctors, it is a reality that it is more difficult for the subject to select a type of surgery and it is inevitable to rely on the words of doctors or counselors for the quality of vision or side effects after a surgery.

DISCLOSURE

Technical Problem

An object is directed to assisting with a doctor's determination or providing objective information about a vision correction surgery to a doctor, a counselor, and a subject.

Another object is directed to recommending a vision correction surgery to a doctor, a counselor, and a subject.

Yet another object is directed to providing a reason for recommendation of a vision correction surgery to a doctor, a counselor, and a subject.

Objects to be provided are not limited to the above-described objects, and objects that are not mentioned will be clearly understood by those of ordinary skill in the art from the present specification and the accompanying drawings.

Technical Solution

According to one aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; when the vision correction surgery is suitable for the subject, predicting whether the vision correction surgery using a laser is available for the subject by inputting a second group data to a second prediction model, the second group data being acquired from the examination data of the subject; when the vision correction surgery using the laser is available for the subject, calculating corneal shape factor prediction values of the subject after a standard vision correction surgery and a custom vision correction surgery by inputting a third group data to a third prediction model so as to be used to determine whether the custom vision correction surgery is necessary, the third group data being acquired from the examination data of the subject; and when the vision correction surgery using the laser is available for the subject, suggesting a vision correction surgery corresponding to the subject by inputting a fourth group data to a fourth prediction model, the fourth group data being acquired from the examination data of the subject, wherein the fourth prediction model is trained based on at least one selected from the group of the examination data of a plurality of patients undergoing a vision correction surgery, vision correction surgeries corresponding to the plurality of patients and visual abilities of the plurality of patients after a vision correction surgery.

According to another aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; when the vision correction surgery is suitable for the subject, predicting whether the vision correction surgery using a laser is available for the subject by inputting a second group data to a second prediction model, the second group data being acquired from the examination data of the subject; when the vision correction surgery using the laser is available for the subject, predicting whether a custom vision correction surgery is necessary for the subject by inputting a third group data to a third prediction model, the third group data being acquired from the examination data of the subject; and when the vision correction surgery using the laser is available for the subject, suggesting a vision correction surgery corresponding to the subject by inputting a fourth group data to a fourth prediction model, the fourth group data being acquired from the examination data of the subject, wherein the predicting whether the custom vision correction surgery is necessary is predicting whether the custom vision correction surgery is necessary based on corneal shape factor prediction values of the subject after a standard vision correction surgery and a custom vision correction surgery, and wherein the fourth prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; when the vision correction surgery is suitable for the subject, predicting whether the vision correction surgery using a laser is available for the subject by inputting a second group data to a second prediction model, the second group data being acquired from the examination data of the subject; and when the vision correction surgery using the laser is available for the subject, suggesting a vision correction surgery corresponding to the subject by inputting a third group data to a third prediction model, the third group data being acquired from the examination data of the subject, wherein the suggesting is suggesting the vision correction surgery based on corneal shape factor prediction values of the subject after a standard vision correction surgery and a custom vision correction surgery, and wherein the third prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; and when the vision correction surgery is suitable for the subject, suggesting a vision correction surgery corresponding to the subject by inputting a second group data to a second prediction model, the second group data being acquired from the examination data of the subject, wherein the suggesting is suggesting the vision correction surgery based on corneal shape factor prediction values of the subject after a standard vision correction surgery and a custom vision correction surgery, and wherein the second prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another aspect, a method for recommending a vision correction surgery using artificial intelligence performed by a computing device may be provided, the method comprising: obtaining an examination data of a subject, the examination data including an interview data and a measurement of an eye characteristics data; and suggesting a vision correction surgery corresponding to the subject by inputting a group data to a prediction model, the group data being acquired from the examination data of the subject, wherein the suggesting is suggesting the vision correction surgery based on corneal shape factor prediction values of the subject after a standard vision correction surgery and a custom vision correction surgery, and wherein the prediction model is trained based on at least one selected from the group of examination data of a plurality of patients undergoing a vision correction surgery, vision correction surgeries corresponding to the plurality of patients and visual abilities of the plurality of patients after a vision correction surgery.

Solutions to be provided are not limited to the above-described solutions, and solutions that are not mentioned will be clearly understood by those of ordinary skill in the art from the present specification and the accompanying drawings.

Advantageous Effects

According to an embodiment, a method of assisting with a doctor's determination or providing objective information about a vision correction surgery to a doctor, a counselor, and a subject, and a device for performing the same can be provided.

According to another embodiment, a vision correction surgery can be recommended to a doctor, a counselor, a subject, or the like using artificial intelligence.

According to yet another embodiment, a reason for recommendation of a vision correction surgery can be provided to a doctor, a counselor, a subject, or the like using artificial intelligence.

Effects to be provided are not limited to the above-described effects, and effects that are not mentioned will be clearly understood by those of ordinary skill in the art from the present specification and the accompanying drawings.

MODES OF THE INVENTION

Figure 1:
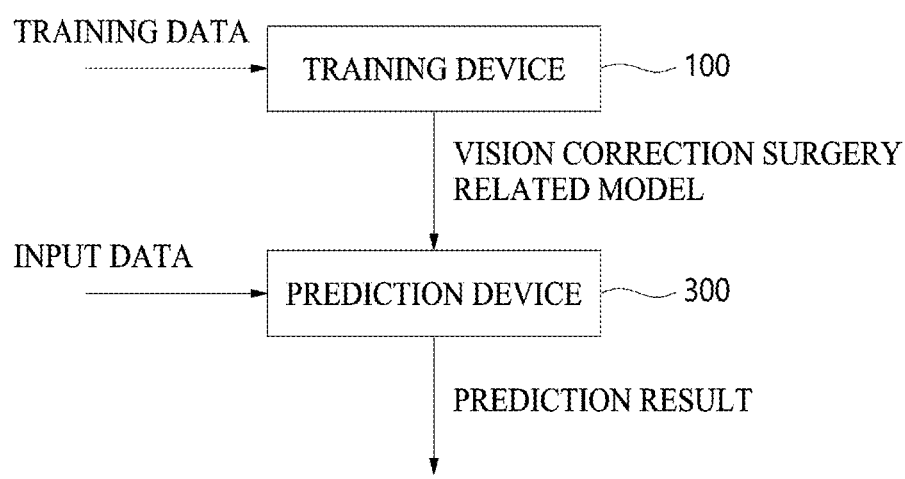
FIG. 1 is a diagram illustrating a vision correction surgery assistance system according to an embodiment.

Since embodiments described in the present specification are intended to clearly explain the spirit of the present invention to those skilled in the art to which the present invention pertains, the present invention is not limited by an embodiments described herein and the scope of the present invention should be construed as including modifications or variations that do not depart from the spirit of the present invention.

Although the terms used herein are selected from among general terms that are currently and widely used in consideration of functions in an embodiments of the present invention, these may be changed according to intentions of those skilled in the art, precedents, or the advent of new technology. However, in a specific case, some terms may be arbitrary selected by applicants. In this case, meanings thereof will be described in detail in a corresponding description of an embodiments of the present invention. Therefore, the terms used herein should be defined based on meanings of the terms and content of this entire specification, rather than simply the terms themselves.

The accompanying drawings of the present specification are for easy explanation of the present invention, and the shapes illustrated in the drawings may be exaggerated and displayed as necessary to aid understanding of the present invention, and thus the present invention is not limited by the drawings.

In the present specification, when detailed descriptions of related well-known technology are deemed to unnecessarily obscure the gist of the invention, they will be omitted. In addition, the terms "first," "second," etc. used in the description of the present specification may refer to different configurations but may correspond to the same configuration.

Hereinafter, a method and device for recommending a vision correction surgery to a subject based on examination data will be described. In particular, a method and device in which a model for recommending a vision correction surgery using artificial intelligence is generated and a vision correction surgery is recommended to a subject using the generated model will be described.

In addition, a method and device for providing visualized information about a vision correction surgery to a subject based on examination data will be described. In particular, a method and device in which a model for providing vision correction surgery visualization information to a subject, such as providing an expected visual ability image after a vision correction surgery using artificial intelligence, predicting a corneal topography image, or analyzing a cause for a prediction result, is generated and the vision correction surgery visualization information is provided to a subject using the generated model will be described.

In the present specification, the vision correction surgery should be broadly interpreted as including a surgery for correcting a visual ability of a patient through corneal cutting using a laser, such as laser-assisted in situ keratomileusis (LASIK), laser-assisted sub-epithelial keratectomy (LASEK), small incision lenticule extraction (SMILE), and the like, and as including a vision correction surgery without using a laser, such as lens implantation.

Further, in the present specification, the visual ability includes a visual ability that can be measured based on determination of a subject and a visual ability that can be measured through eye examination, etc. For example, the visual ability may be measured using an eye chart. Alternatively, the visual ability may include lower-order aberrations, which are basic refractive errors such as nearsightedness, farsightedness, and astigmatism, and higher-order aberrations, such as spherical aberration, coma aberration, trefoil aberration, and the like. Further, the visual ability may include uncorrected visual ability and corrected visual ability.

According to one aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; when the vision correction surgery is suitable for the subject, predicting whether the vision correction surgery using a laser is available for the subject by inputting a second group data to a second prediction model, the second group data being acquired from the examination data of the subject; when the vision correction surgery using the laser is available for the subject, calculating corneal shape factor prediction values of the subject after a standard vision correction surgery and a custom vision correction surgery by inputting a third group data to a third prediction model so as to be used to determine whether the custom vision correction surgery is necessary, the third group data being acquired from the examination data of the subject; and when the vision correction surgery using the laser is available for the subject, suggesting a vision correction surgery corresponding to the subject by inputting a fourth group data to a fourth prediction model, the fourth group data being acquired from the examination data of the subject, wherein the fourth prediction model is trained based on at least one selected from the group of the examination data of a plurality of patients undergoing a vision correction surgery, vision correction surgeries corresponding to the plurality of patients and visual abilities of the plurality of patients after a vision correction surgery.

Herein, the suggesting may be suggesting the vision correction surgery based on a predicted visual ability value of the subject after a vision correction surgery.

Herein, the suggesting may be suggesting the vision correction surgery by calculating the predicted visual ability value of the subject after a vision correction surgery each corresponding to the plurality of vision correction surgeries.

Herein, the suggesting may be suggesting the vision correction surgery by calculating a plurality of predicted visual ability values corresponding to a plurality of different time points.

Herein, the method may further comprise predicting whether the custom vision correction surgery is necessary for the subject based on the calculated corneal shape factor prediction value after the standard vision correction surgery and the calculated corneal shape factor prediction value after the custom vision correction surgery.

Herein, the suggesting may be suggesting the vision correction surgery based on the calculated corneal shape factor prediction value after the standard vision correction surgery and the calculated corneal shape factor prediction value after the custom vision correction surgery.

Herein, when the fourth prediction model is trained by considering preferences of the plurality of patients for a vision correction surgery, the fourth group data may include a preference of the subject for a vision correction surgery.

Herein, at least one selected from the group of the first prediction model, the second prediction model, the third prediction model and the fourth prediction model may include a plurality of sub-models, and calculate a result based on results of the plurality of sub-models.

Herein, at least one selected from the group of the first group data, the second group data, the third group data and the fourth group data may include at least a portion of the examination data of the subject as it is, or include a new type of data calculated from at least a portion of the examination data of the subject.

Herein, the corneal shape factor prediction value may include at least one selected from the group of a predicted index of height decentration (IHD), a predicted index of surface variance (ISC) and a predicted index of vertical asymmetry (IVA).

Herein, the examination data may further includes genetic information.

According to another aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; when the vision correction surgery is suitable for the subject, predicting whether the vision correction surgery using a laser is available for the subject by inputting a second group data to a second prediction model, the second group data being acquired from the examination data of the subject; when the vision correction surgery using the laser is available for the subject, predicting whether a custom vision correction surgery is necessary for the subject by inputting a third group data to a third prediction model, the third group data being acquired from the examination data of the subject; and when the vision correction surgery using the laser is available for the subject, suggesting a vision correction surgery corresponding to the subject by inputting a fourth group data to a fourth prediction model, the fourth group data being acquired from the examination data of the subject, wherein the predicting whether the custom vision correction surgery is necessary is predicting whether the custom vision correction surgery is necessary based on corneal shape factor prediction values of the subject after a standard vision correction surgery and a custom vision correction surgery, and wherein the fourth prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; when the vision correction surgery is suitable for the subject, predicting whether the vision correction surgery using a laser is available for the subject by inputting a second group data to a second prediction model, the second group data being acquired from the examination data of the subject; and when the vision correction surgery using the laser is available for the subject, suggesting a vision correction surgery corresponding to the subject by inputting a third group data to a third prediction model, the third group data being acquired from the examination data of the subject, wherein the suggesting is suggesting the vision correction surgery based on corneal shape factor prediction values of the subject after a standard vision correction surgery and a custom vision correction surgery, and wherein the third prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another aspect, a method for recommending a vision correction surgery using artificial intelligence performed by a computing device may be provided, the method comprising: obtaining an examination data of a subject, the examination data including an interview data and a measurement of an eye characteristics data; predicting whether the vision correction surgery is suitable for the subject by inputting a first group data to a first prediction model, the first group data being acquired from the examination data of the subject; and when the vision correction surgery is suitable for the subject, suggesting a vision correction surgery corresponding to the subject by inputting a second group data to a second prediction model, the second group data being acquired from the examination data of the subject, wherein the suggesting is suggesting the vision correction surgery based on corneal shape factor prediction values of the subject after a standard vision correction surgery and a custom vision correction surgery, and wherein the second prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another aspect, a method for recommending a vision correction surgery using artificial intelligence performed by a computing device may be provided, the method comprising: obtaining an examination data of a subject, the examination data including an interview data and a measurement of an eye characteristics data; and suggesting a vision correction surgery corresponding to the subject by inputting a group data to a prediction model, the group data being acquired from the examination data of the subject, wherein the suggesting is suggesting the vision correction surgery based on corneal shape factor prediction values of the subject after a standard vision correction surgery and a custom vision correction surgery, and wherein the prediction model is trained based on at least one selected from the group of examination data of a plurality of patients undergoing a vision correction surgery, vision correction surgeries corresponding to the plurality of patients and visual abilities of the plurality of patients after a vision correction surgery.

According to yet another embodiment, a method of providing an expected visual ability image after a vision correction surgery using artificial intelligence performed by a computing device may be provided, the method including: obtaining examination data of a subject, the examination data including interview data and a measurement of eye characteristic data; calculating prediction values of pieces of the eye characteristic data of the subject after the vision correction surgery by inputting first group data obtained from the examination data of the subject to a first prediction model, the prediction values of the pieces of the eye characteristic data including at least one of a predicted visual ability value and a corneal shape factor prediction value; and generating an expected visual ability image based on the prediction values of the pieces of the eye characteristic data, wherein the first prediction model may be trained based on at least one among measurements of pieces of eye characteristic data before a surgery of a plurality of patients who have undergone vision correction surgeries, surgery parameters of the vision correction surgeries performed on the plurality of patients, and measurements of the pieces of the eye characteristic data after a surgery of the plurality of patients.

Herein, the generating of the expected visual ability image may include calculating or selecting a filter based on the prediction values of the pieces of the eye characteristic data and applying the filter to an original image to generate the expected visual ability image.

Herein, the prediction values of the pieces of the eye characteristic data may include a first prediction value of the eye characteristic data and a second prediction value of the eye characteristic data, and the expected visual ability image may include a first expected visual ability image, which is generated based on the first prediction value of the eye characteristic data, and a second expected visual ability image which is generated based on the second prediction value of the eye characteristic data and different from the first expected visual ability image.

Herein, the first prediction value of the eye characteristic data and the second prediction value of the eye characteristic data may correspond to a prediction value of eye characteristic data after a standard vision correction surgery and a prediction value of eye characteristic data after a custom vision correction surgery, respectively, and the first expected visual ability image and the second expected visual ability image may correspond to an expected visual ability image after a standard vision correction surgery and an expected visual ability image after a custom vision correction surgery, respectively.

Herein, the expected visual ability image may include information about at least one selected from the group of clarity of vision, light bleeding, contrast sensitivity, night vision, glare, double vision, and afterimages of the subject which are expected after the vision correction surgery.

Herein, the method of providing the expected visual ability image may further include predicting a corneal topography image of the subject after the vision correction surgery by inputting second group data obtained from the examination data of the subject to a second prediction model, wherein the second prediction model may be trained based on at least one selected from the group of corneal topography images before surgeries of a plurality of patients who have undergone vision correction surgeries, the surgery parameters of the vision correction surgeries performed on the plurality of patients, and corneal topography images after surgeries of the plurality of patients.

Herein, the method of providing the expected visual ability image may further include calculating a dependency of the prediction value of the eye characteristic data on the first group data.

Herein, the prediction values of the pieces of the eye characteristic data may include the first prediction value of the eye characteristic data and the second prediction value of the eye characteristic data, the dependency may include a dependency coefficient corresponding to at least one piece of the first group data, and the dependency coefficient may include a first dependency coefficient corresponding to the first prediction value of the eye characteristic data and a second dependency coefficient which corresponds to the second prediction value of the eye characteristic data and is different from the first dependency coefficient.

Herein, the first prediction value of the eye characteristic data and the second prediction value of the eye characteristic data may correspond to the prediction value of the eye characteristic data after the standard vision correction surgery and the prediction value of the eye characteristic data after the custom vision correction surgery, respectively, and the first dependency coefficient and the second dependency coefficient may correspond to a dependency of the prediction value of the eye characteristic data on the first group data after the standard vision correction surgery and a dependency of the prediction values of the eye characteristic data on the first group data after the custom vision correction surgery, respectively.

Herein, the method of providing the expected visual ability image may further include outputting, among the dependency coefficients, the dependency coefficient greater than a predetermined value or outputting a predetermined number of dependency coefficients.

Herein, the corneal shape factor prediction value may include at least one selected from the group of a predicted index of height decentration (IHD), a predicted index of surface variance (ISV), and a predicted index of vertical asymmetry (IVA).

Herein, the predicted visual ability value may include at least one of predicted lower-order aberrations or predicted high-order aberrations.

A vision correction surgery assistance system according to an embodiment may include a training device and a prediction device. Here, the training device and the prediction device may be a computing device including at least one control unit. Examples of the computing device may include a desktop computer, a laptop computer, a tablet PC, and a smartphone, but not limited thereto.

FIG. 1 is a diagram illustrating a vision correction surgery assistance system 10 according to an embodiment. Referring to FIG. 1, a training device 100 may train and/or generate a model (hereinafter, referred to as a "vision correction surgery related model") in which information about a vision correction surgery is generated based on training data. Here, the training data is data that is necessary for training and/or generating a vision correction surgery related model, such as numbers, characters, images, and the like, with no limitation on an expression method thereof. For example, the training data may include examination data of a patient who has undergone the vision correction surgery and surgery parameters.

A prediction device 300 may calculate a prediction result, which is information about a vision correction surgery, based on the vision correction surgery related model generated by the training device 100 and input data. Here, the input data is data that is a basis for calculating a prediction result, such as a number, a character, an image, or the like, with no limitation on an expression method thereof.

Specific examples of the training data, the input data, the prediction result, and the vision correction surgery related model will be described below.

In FIG. 1, the training device 100 and the prediction device 300 are illustrated as being separate devices, but the training device 100 and the prediction device 300 may be the same device. For example, in the same device, a vision correction surgery related model may be trained and/or generated and a prediction result may be calculated using the model. Alternatively, at least some components of the training device 100 and at least some components of the prediction device 300 may be the same.

Further, the vision correction surgery assistance system according to an embodiment may include a plurality of training devices and/or a plurality of prediction devices.

Figure 2:
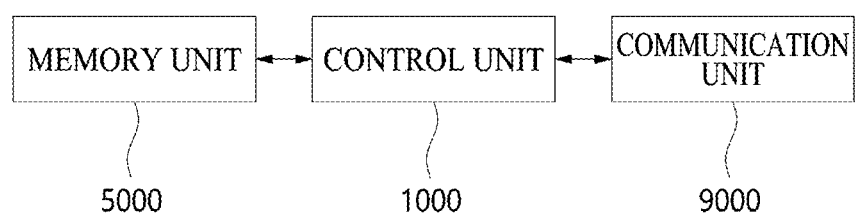
FIG. 2 is a diagram for describing a training device/a prediction device according to an embodiment.

FIG. 2 is a diagram for describing a training device/a prediction device according to an embodiment. Referring to FIG. 2, the training device/the prediction device according to an embodiment may include a memory unit 5000 and a control unit 1000.

The training device/the prediction device according to an embodiment may include the control unit 1000 for controlling operations thereof. The control unit 1000 may include a central processing unit (CPU), a random access memory (RAM), a graphic processing unit (GPU), one or more microprocessors, and one or more electronic parts capable of processing input data according to predetermined logic.

The control unit 1000 may read system programs stored in the memory unit 5000 and various processing programs. For example, the control unit 1000 may develop data handling process and the like for executing training and prediction operations of a vision correction surgery related model, which will be described below, in the RAM and perform various processes according to the developed programs. For example, the control unit 1000 may perform the training of the vision correction surgery related model. As another example, the control unit 1000 may use the vision correction surgery related model to generate a prediction result.

The training device/the prediction device according to an embodiment may include the memory unit 5000. The memory unit 5000 may store data that is necessary for training, a training model, and a trained vision correction surgery related model. The memory unit 5000 may store parameters, variables, and the like of the vision correction surgery related model.

The memory unit 5000 may be implemented as a non-volatile semiconductor memory, a hard disk, a flash memory, a RAM, a read-only memory (ROM), an electrically erasable programmable read-only memory (EEPROM), a tangible non-volatile recording medium, or the like.

The memory unit 5000 may store various types of processing programs, parameters used for performing processing of the programs, result data of the processing, or the like. For example, the memory unit 5000 may store the data handling process programs for performing the training and prediction operations of the vision correction surgery related model, which will be described below, diagnostic process programs, parameters used for executing each program, and data (e.g., processed data or a prediction result) obtained from the execution of the programs.

The training device and/or the prediction device according to an embodiment may further include a communication unit 9000. The communication unit 9000 may communicate with an external device. For example, the communication unit 9000 of the training device may communicate with the communication unit 9000 of the prediction device. The communication unit 9000 may perform wired or wireless communication. The communication unit 9000 may perform bi-directional or unidirectional communication.

The training device/the prediction device illustrated in FIG. 2 is only exemplary, and the configuration of the training device and/or the prediction device is not limited thereto.

Figure 3:
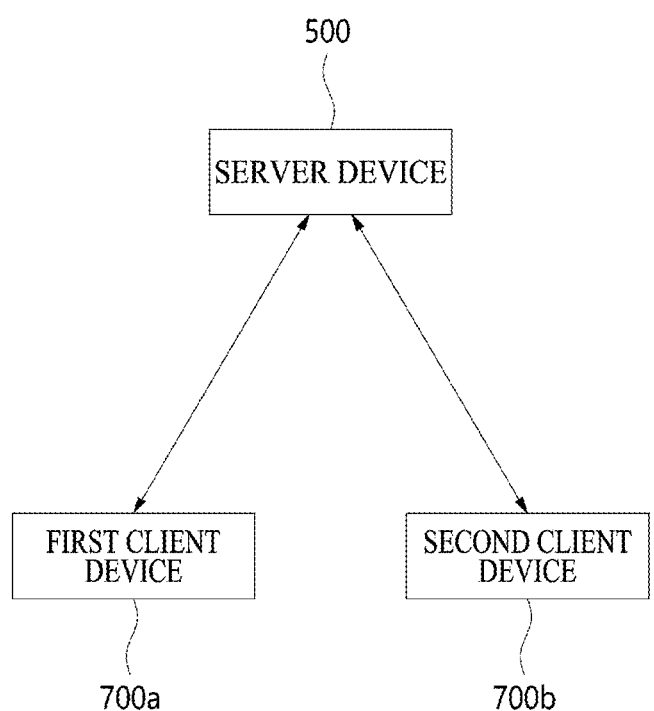
FIG. 3 is a diagram for describing a server device and client devices according to an embodiment.

The vision correction surgery assistance system according to an embodiment may include a server device and a client device. FIG. 3 is a diagram for describing a server device 500 and client devices 700a and 700b according to an embodiment.

The server device 500 according to an embodiment may correspond to the training device/the prediction device described above. The server device 500 according to an embodiment may train, store, and/or execute the vision correction surgery related model.

The client devices 700a and 700b according to an embodiment may correspond to the training device/the prediction device described above. The client devices 700a and 700b according to an embodiment may train, store, and/or execute the vision correction surgery related model.

The client devices 700a and 700b according to an embodiment may obtain the trained vision correction surgery related model from the server device 500. For example, the client devices 700a and 700b may download the vision correction surgery related model from the server device 500 via a network.

The server device 500 according to an embodiment may calculate a prediction result based on input data obtained from the client devices 700a and 700b. For example, the client devices 700a and 700b may receive information about a subject and transmit the information to the server device 500, and the server device 500 may calculate a prediction result using the vision correction surgery related model based on the information about the subject. The server device 500 according to an embodiment may obtain the input data from the plurality of client devices 700a and 700b.

The server device 500 according to an embodiment may transmit the calculated prediction result to the client devices 700a and 700b. For example, the client devices 700a and 700b may provide the prediction result obtained from the server device 500 to a doctor, a counselor, and a subject. The server device 500 according to an embodiment may obtain feedback from the client devices 700a and 700b. The server device 500 according to an embodiment may transmit the prediction result to the plurality of client devices 700a and 700b.

The client devices 700a and 700b according to an embodiment may request the prediction result from the server device 500.

The client devices 700a and 700b according to an embodiment may transmit the inputted data to the server device 500. The client devices 700a and 700b according to an embodiment may change some pieces of the inputted data and transmit the changed data to the server device 500. The client devices 700a and 700b according to an embodiment may provide the prediction result obtained from the server device 500 to the doctor, the counselor, and the subject. The client devices 700a and 700b according to an embodiment may change at least a portion of the prediction result obtained from the server device 500 and provide the changed prediction result to the doctor, the counselor, and the subject.

In FIG. 3, a relationship between one server device 500 and two client devices 700a and 700b is illustrated, but not limited thereto, and the relationship may be applied to one or more server devices 500 and one or more client devices 700a and 700b.

Figure 4:
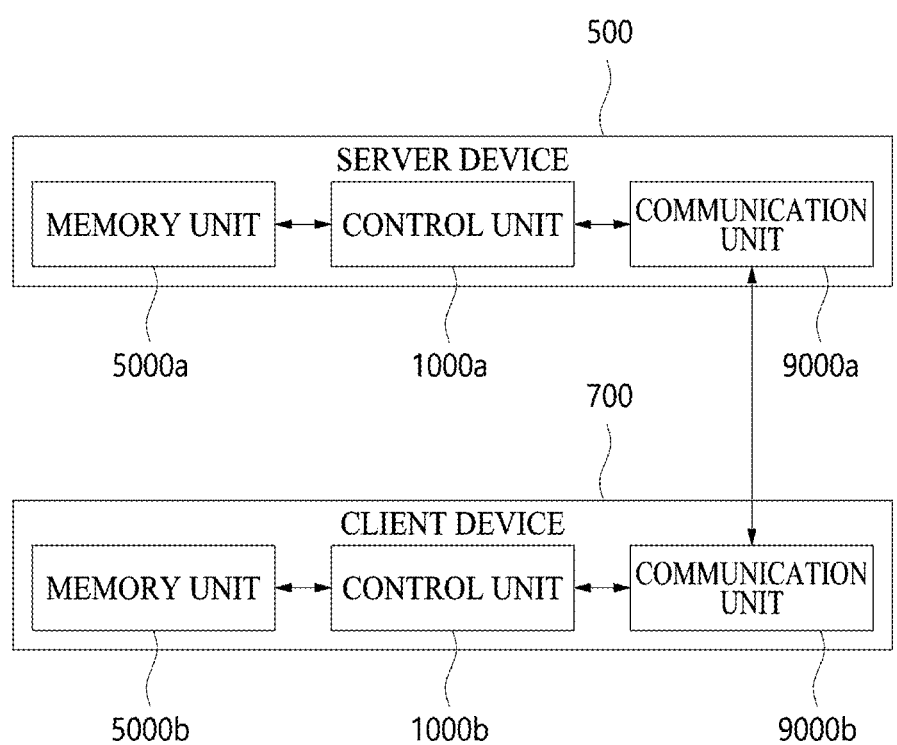
FIG. 4 is a diagram illustrating configurations of a server device and a client device according to an embodiment.

FIG. 4 is a diagram illustrating configurations of a server device 500 and a client device 700 according to an embodiment. Referring to FIG. 4, the server device 500 and the client device 700 may include a memory unit 5000a, 5000b, a control unit 1000a, 1000b, and a communication unit 9000a, 9000b. The server device 500 and the client device 700 may transmit and obtain information through the communication units 9000a and 9000b, respectively. For example, the client device 700 may obtain a trained vision correction surgery related model from the communication unit 9000a of the server device 500 through the communication unit 9000b thereof. As another example, the client device 700 may transmit input data to the communication unit 9000a of the server device 500 through the communication unit 9000b thereof, and the server device 500 may transmit a prediction result to the communication unit 9000b of the client device 700 through the communication unit 9000a thereof.

As described above, the vision correction surgery related model is a model in which various pieces of information that can be considered during, before, and after a vision correction surgery are generated.

Figure 5:
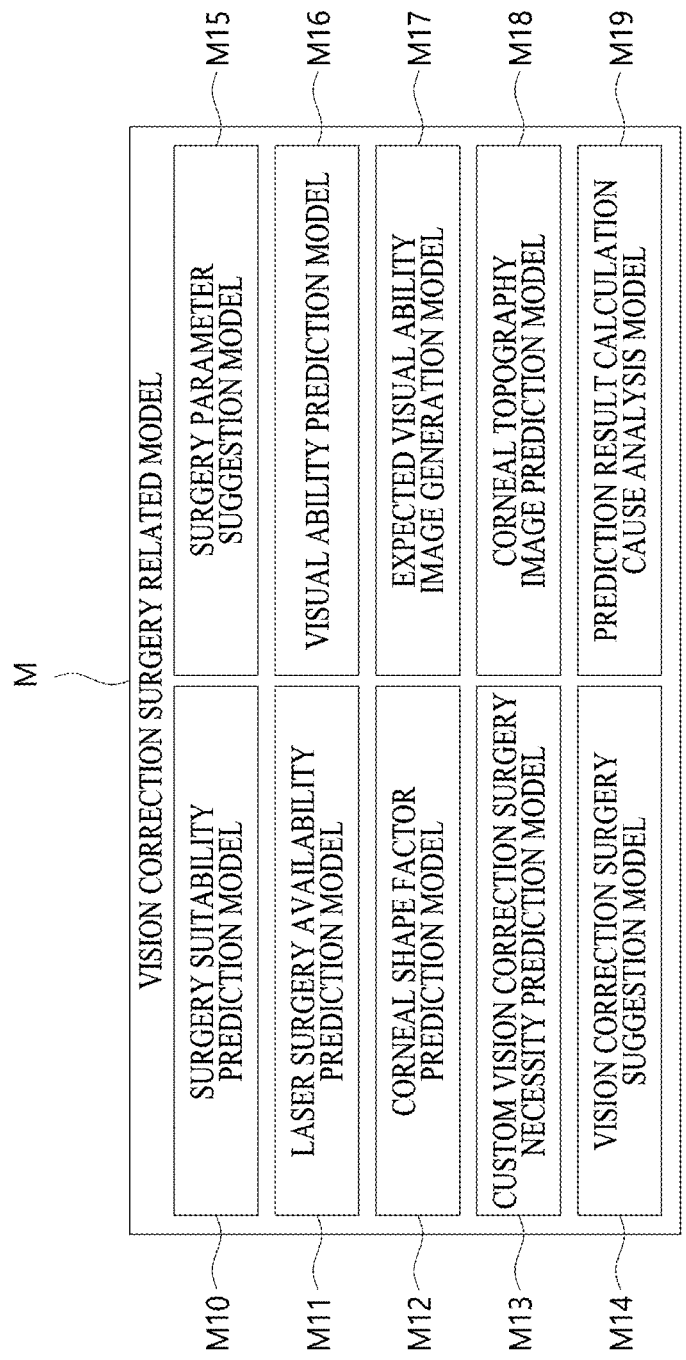
FIG. 5 is a diagram illustrating a vision correction surgery related model according to an embodiment.

FIG. 5 is a diagram illustrating a vision correction surgery related model M according to an embodiment. Referring to FIG. 5, the vision correction surgery related model M may include a surgery suitability prediction model M10, a laser surgery availability prediction model M11, a corneal shape factor prediction model M12, a custom vision correction surgery necessity prediction model M13, a vision correction surgery suggestion model M14, a surgery parameter suggestion model M15, a visual ability prediction model M16, an expected visual ability image generation model M17, a corneal topography image prediction model M18, and a prediction result calculation cause analysis model M19. A detailed description of each model will be given below.

At least part of the models of the vision correction surgery related model M may be trained and/or generated in the same training device. For example, the surgery suitability prediction model M10 and the laser surgery availability prediction model M11 may be trained and/or generated in the same training device. Alternatively, at least part of the models of the vision correction surgery related model M may be trained and/or generated in different training devices.

At least part of the models of the vision correction surgery related model M may be executed in the same prediction device. For example, the surgery suitability prediction model M10 and the laser surgery availability prediction model M11 may be executed in the same prediction device. Alternatively, at least part of the models of the vision correction surgery related model M may be executed in different prediction devices.

The vision correction surgery related model according to an embodiment may be trained and/or implemented using an artificial intelligence model/algorithm, and there is no limitation on a training and/or implementation method thereof. For example, the vision correction surgery related model may be trained and/or implemented using various machine learning models/algorithms and deep learning models/algorithms, such as a classification algorithm, a regression algorithm, supervised learning, unsupervised learning, reinforcement learning, support vector machine, a decision tree, random forests, least absolute shrinkage and selection operator (LASSO), AdaBoost, XGBoost, an artificial neural network, and the like.

The vision correction surgery related model according to an embodiment may be trained and/or generated through a training operation. The vision correction surgery related model trained and/or generated through the training operation may calculate a prediction result through a prediction operation.

Figure 6:
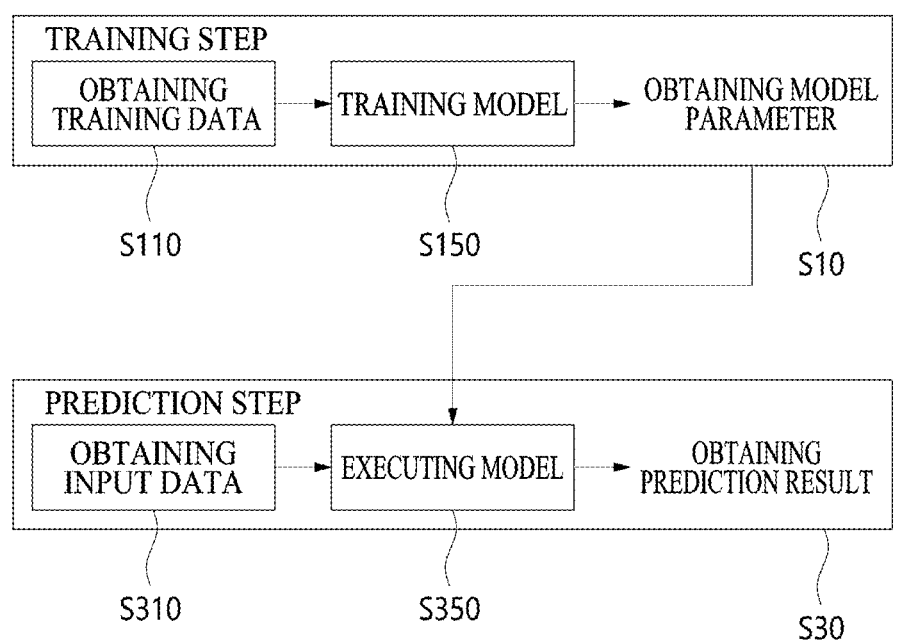
FIG. 6 is a diagram for describing a training operation and a prediction operation of a vision correction surgery related model according to an embodiment.

FIG. 6 is a diagram for describing a training operation S10 and a prediction operation S30 of a vision correction surgery related model according to an embodiment. Referring to FIG. 6, the training operation S10 may include an operation S110 of obtaining training data and an operation S150 of training a model.

The operation S110 of obtaining the training data may be an operation of obtaining, by a training device, the training data, which is data for training and/or generating the vision correction surgery related model.

The operation S150 of training the model may be an operation of training and/or generating the vision correction surgery related model. In the operation S150 of training the model, the training device may train and/or generate a model based on the training data obtained in the operation of obtaining the training data. For example, model parameters constituting the vision correction surgery related model may be changed in the operation S150 of training the model. The accuracy of the model may be improved according to a change in the parameters.

The vision correction surgery related model may be trained based on information about a vision correction surgery of a patient who has undergone the vision correction surgery. For example, the model may be trained based on at least one selected from the group of examination data before a vision correction surgery of a plurality of patients who have undergone the vision correction surgery, surgery parameters of the vision correction surgery performed on the plurality of patients, and examination data after a vision correction surgery of the plurality of patients.

Referring to FIG. 6, the prediction operation S30 may include an operation S310 of obtaining input data and an operation S350 of executing a model.

The operation S310 of obtaining the input data may be an operation of obtaining, by the prediction device, the input data, which is data that can be used to calculate a prediction result using the vision correction surgery related model.

The operation S350 of executing the model may be an operation of calculating the prediction result based on the vision correction surgery related model trained and/or generated in the training operation S10 and the input data. For example, the prediction device may output the prediction result based on the input data and the model parameters obtained from the training device.

The input data of the vision correction surgery related model may include all pieces of obtained information about a subject. Alternatively, the input data may include at least part of the obtained information about the subject. Further, the input data may be the same or different according to the vision correction surgery related model.

The prediction result of the vision correction surgery related model may vary according to the training data. Alternatively, the accuracy of the vision correction surgery related model may vary according to the training data.

The prediction result may vary according to a type of a true value included in the training data. For example, the prediction result may vary according to whether the true value considers subjective intention of the subject. Here, the subjective intention of the subject may include a preference, such as whether the subject prefers a specific vision correction surgery, and an ability to pay a cost, such as how much money can be paid for the vision correction surgery. When the subjective intention of the subject is not considered, the prediction result may be a medically suggested result. On the other hand, when the subjective intention of the subject is considered, the prediction result may be the same as or different from the medically suggested result.

When first training data and second training data are obtained from different hospitals or from different doctors or are pieces of training data at different times, a first model trained and/or generated based on the first training data and a second model trained and/or generated based on the second training data may be different from each other. As a result, a first prediction result output from the first model and a second prediction result output from the second model may be different from each other. Further, the accuracy of the first model and the accuracy of the second model may be different from each other.

However, even when the pieces of training data are different, the same vision correction surgery related model may be trained and/or generated. Alternatively, even when the vision correction surgery related model is trained and/or generated based on pieces of different training data, the same prediction result may be calculated.

The training data, the input data, and the prediction result (hereinafter, referred to as "input/output data") may include examination data and variables such as surgery parameters. The examination data and the surgery parameter may be expressed in various ways, such as numbers, characters, images, and the like, and there is no limitation on an expression method thereof. Further, the images are two-dimensional (2D) images or three-dimensional (3D) images with no limitation on their dimensions.

The examination data may include interview data, which is information obtained by asking questions without going through equipment or inspection, eye characteristic data, which is information about eyes obtained through equipment or inspection, and genetic information.

The interview data may include variables, such as demographic characteristics, such as gender, age, race, living environment such as where the subject lives, occupation, income, educational background, education, and family size of the subject, medical history and family history of the subject, such as hypertension, diabetes, and the like, and a preference of the subject with regard to a vision correction surgery.

The eye characteristic data may include all types of information about an eye. For example, the eye characteristic data may include variables, such as a visual ability, intraocular pressure, and/or a result of retina examination.

The eye characteristic data may include information about a physical shape of the eye. For example, the eye characteristic data may include variables, such as a white-to-white (WTW) distance, an angle-to-angle (ATA) distance, an internal anterior chamber depth (ACD), a sulcus-to-sulcus (STS) distance, a size of a pupil, and the like. As another example, the eye characteristic data may include information about a shape of a cornea, such as a corneal shape factor, a corneal topographic image, and the like. Here, the corneal shape factor is a numerical value representing the physical shape of the cornea and may include variables, such as an index of surface variance (ISV), an index of vertical asymmetry (IVA), a keratoconus index (KI), a central keratoconus index (CKI), a minimum radius of curvature (Rmin), an index of height asymmetry (IHA), an index of height decentration (IHD), a central cornea thickness, and the like. Further, the corneal topography image is an image related to the shape of the cornea and may include a corneal topography map, a corneal anterior curvature image, a corneal posterior curvature image, a corneal thickness map, and the like.

The eye characteristic data may be obtained through tomography, topography, optical coherence tomography (OCT), ultrasound biomicroscopy (UBM) equipment, such as Pentacam, CASIA2, AL-Scan, OQAS, etc., but not limited thereto. The information that can be obtained through the above equipment and similar equipment thereto and information derived therefrom may be included in the eye characteristic data.

The genetic information may be obtained through genetic testing or the like. The genetic information may be used to determine whether the vision correction surgery is suitable for the subject. Alternatively, the genetic information may be used to predict side effects after vision correction surgery. For example, whether corneal dystrophy is present may be predicted using the genetic information.

The surgery parameters are variables related to the performance of the vision correction surgery and may include variables that can be changed during the vision correction surgery, such as a type of the vision correction surgery, such as LASIK, LASEK, SMILE, lens implantation, a standard vision correction surgery, a custom vision correction surgery, or the like, a corneal flap thickness, a corneal flap diameter, a flap side cut angle, a corneal cutting profile, an eye suction time, an optic zone, a hinge structure, such as a hinge position, a hinge angle, and a hinge width, and the like.

The standard vision correction surgery may refer to a vision correction surgery for correcting lower-order aberrations, and the custom vision correction surgery may refer to a vision correction surgery for correcting lower-order aberrations and high-order aberrations.

The types of surgery parameters considered according to the patient of the standard vision correction surgery and the patient of the custom vision correction surgery may be different from each other. For example, the types of surgery parameters considered according to the patient of the custom vision correction surgery may include the types of surgery parameters considered according to the patient of the standard vision correction surgery.

The number of surgery parameters that are changed according to the patient of the standard vision correction surgery may be different from the number of surgery parameters that are changed according to the patient of the custom vision correction surgery. The standard vision correction surgery and the custom vision correction surgery may be distinguished by the number of surgery parameters that are changed according to the patient. The number (hereinafter, referred to as a "reference value") of surgery parameters that are changed according to the patient to distinguish the standard vision correction surgery from the custom vision correction surgery may be a predetermined value. For example, when the number of surgery parameters that are changed according to the patient is greater than or equal to the reference value, a custom vision correction surgery may be performed, and when the number of surgery parameters is less than the reference value, a standard vision correction surgery may be performed.

The standard vision correction surgery and the custom vision correction surgery may vary according to a hospital where the vision correction surgery is performed, a doctor, and/or timing. For example, the reference value may vary according to the hospital, the doctor, and/or the timing.

The custom vision correction surgery may include Contoura vision and wavefront LASIK.

The quality of vision when the custom vision correction surgery is performed may be improved as compared to when the standard vision correction surgery is performed. The quality of vision is a term that comprehensively refers to whether vision is good or bad and may be determined based on not only vision measured through an eye chart, lower-order aberrations, and the high-order aberrations but also clarity of vision, light bleeding, contrast sensitivity, night vision, glare, double vision, afterimages, and other discomforts.

The input/output data may include not only measurements that can be obtained/measured through an examination by interview and an examination but also predicted values that can be calculated through the vision correction surgery related model. For example, the eye characteristic data may include not only measurements of eye characteristic data before a vision correction surgery obtained/measured through examination but also prediction values of eye characteristic data after a vision correction surgery calculated through the vision correction surgery related model.

The input/output data may be pre-processed and input to the vision correction surgery related model. For example, the training device may pre-process the obtained input/output data and then use the obtained input/output data for the training of the vision correction surgery related model. Alternatively, the prediction device may pre-process the obtained input/output data and then input the obtained input/output data to the vision correction surgery related model to calculate a prediction result.

The pre-processing should be broadly interpreted to include all changes applied to the input/output data and is not limited to examples disclosed in the present specification.

The pre-processing may include selecting at least part of variables included in the input/output data, such as feature selection. For example, the pre-processing may include t-test, Gini index, information gain, relief, DistAUC, signal to noise, MRMR, Fisher score, Laplacian score, SPEC, and the like.

The pre-processing may include generating new variables from at least part of the variables included in the input/output data, such as feature extraction. For example, the pre-processing may include principle component analysis, linear discriminant analysis, canonical correlation analysis, singular value decomposition, ISOMAP, locally linear embedding, and the like. As another example, the pre-processing may include generating a spectrum from numerical values or generation of an image from numerical values.

The pre-processing may include a processing method when a variable required by the vision correction surgery related model (or the training device and/or the prediction device) is not included in the input/output data, such as missing value processing. For example, the pre-processing may include processing of a missing value as an average of the corresponding variable or processing the missing value as a mode.

Through the pre-processing, the accuracy of the vision correction surgery related model may be improved. As an example, the accuracy of a vision correction surgery related model including feature selection may be higher than that of a model excluding feature selection. As another example, the accuracy of a vision correction surgery related model in which an image is generated from a numerical value and a prediction result is calculated based on the image may be higher than the accuracy of a vision correction surgery related model in which a prediction result is calculated based on the numerical value.

Figure 7:
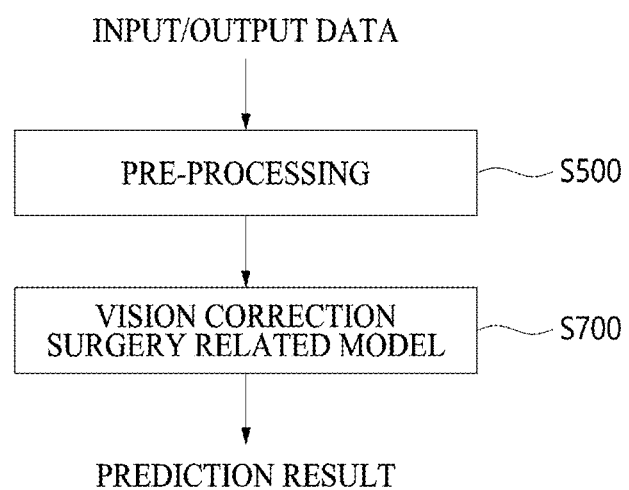
FIG. 7 is a diagram illustrating pre-processing of input/output data according to an embodiment.

FIG. 7 is a diagram illustrating pre-processing of input/output data according to an embodiment. Referring to FIG. 7, the input/output data may be input to a vision correction surgery related model through a pre-processing operation S500. The vision correction surgery related model may calculate a prediction result based on the pre-processed input/output data (S700).

The vision correction surgery related model may include a plurality of sub-models. The plurality of sub-models may calculate the prediction result based on input data.

The vision correction surgery related model may include a model, such as an ensemble model and the like, in which sub-models are connected in series and/or in parallel.

The vision correction surgery related model may include a plurality of sub-models connected in series. Here, the sub-models connected in series may mean that an output of at least one sub-model is calculated based on an output of at least another sub-model, such as an output of a first sub-model being an input of a second sub-model, and the like. Alternatively, the sub-models connected in series may mean that a plurality of sub-models should be sequentially executed to obtain a prediction result from input data through the vision correction surgery related model.

Figure 8:
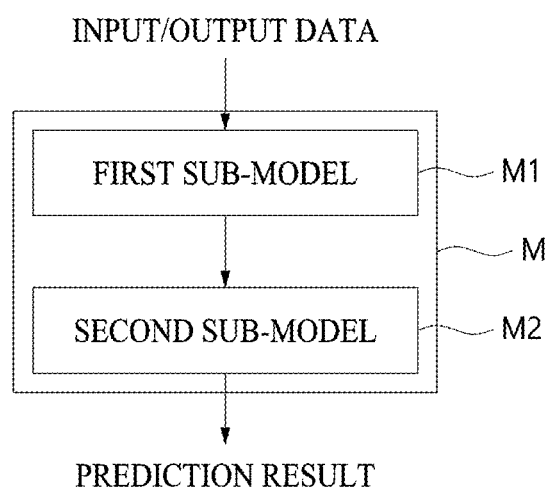
FIG. 8 is a diagram illustrating a vision correction surgery related model including sub-models connected in series according to an embodiment.

FIG. 8 is a diagram illustrating a vision correction surgery related model M including sub-models M1 and M2 connected in series according to an embodiment. Referring to FIG. 8, the vision correction surgery related model M may include a first sub-model M1 and a second sub-model M2 connected in series. The first sub-model M1 may calculate an output based on input/output data, and the second sub-model M2 may calculate a prediction result based on the output of the first sub-model M1.

The vision correction surgery related model may include a plurality of sub-models connected in parallel. Here, the sub-models connected in parallel may mean that an output of one sub-model does not affect an output of another sub-model, such as that an output of a first sub-model does not depend on an output of a second sub-model, and the like.

Inputs of the plurality of sub-models connected in parallel may be the same. Alternatively, the inputs of the plurality of sub-models connected in parallel may be different. For example, first examination data input to the first sub-model may be different from second examination data input to the second sub-model.

The first examination data may include at least some variables different from those of the second examination data. For example, the first examination data may include a preference with regard to a vision correction surgery, but the second examination data may not include the preference with regard to the vision correction surgery.

The first examination data may have the same type of variable as the second examination data, but the variables may have different values. For example, the first examination data and the second examination data may include a cornea thickness, but methods of obtaining numerical values of the cornea thickness are different (e.g., the cornea thickness is measured with different devices) so that the numerical values may be different.

The vision correction surgery related model may include an output sub-model in which an output is calculated based on outputs of the plurality of sub-models connected in parallel. As an example, when the outputs of the plurality of sub-models are the same, the output sub-model may provide the same output. As another example, when the outputs of the plurality of sub-models are different, the output sub-model may output a result in consideration of the outputs of the plurality of sub-models at a predetermined ratio or may provide a specific output among the plurality of outputs. As yet another example, the output sub-model may output a result generated based on the outputs of the plurality of sub-models.

Figure 9:
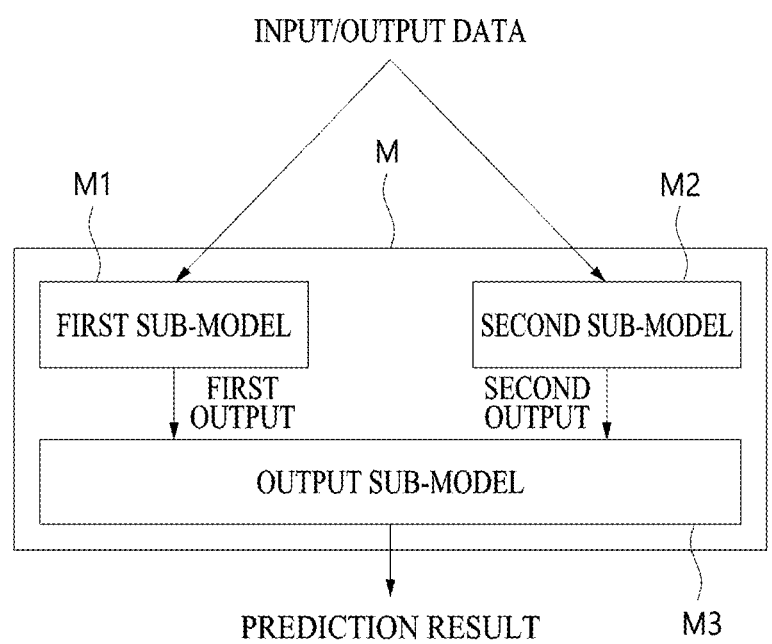
FIG. 9 is a diagram illustrating a vision correction surgery related model including sub-models connected in parallel according to an embodiment.

FIG. 9 is a diagram illustrating a vision correction surgery related model M including sub-models M1 and M2 connected in parallel according to an embodiment. Referring to FIG. 9, the vision correction surgery related model M may include a first sub-model M1 and a second sub-model M2 connected in parallel. Further, the vision correction surgery related model M may include an output sub-model M3 in which an output is calculated based on outputs of the first sub-model M1 and the second sub-model M2. The first sub-model M1 and the second sub-model M2 may calculate a first output and a second output, respectively, based on input/output data, and the output sub-model M3 may calculate a prediction result based on the first output and the second output.

An example of the vision correction surgery related model including the sub-models connected in parallel may include an ensemble model, but not limited thereto.

Hereinafter, individual examples of the vision correction surgery related model will be described.

The surgery suitability prediction model may predict whether a vision correction surgery is suitable for a subject. The surgery suitability prediction model may predict surgery suitability based on input data.

The suitability for the vision correction surgery may refer to medical suitability. Accordingly, the input data of the surgery suitability prediction model may not include a preference of the subject with regard to the vision correction surgery. Alternatively, the surgery suitability prediction model may predict the surgery suitability without consideration of the preference of the subject with regard to the vision correction surgery.

The surgery suitability may include whether surgery is possible and whether surgery is necessary. As an example, the surgery suitability prediction model may determine that a subject who does not need surgery because of good vision is unsuitable for surgery. As another example, the surgery suitability prediction model may determine that a subject who cannot improve his or her vision through a vision correction surgery is unsuitable for surgery.

The surgery suitability may be output as suitable or unsuitable for surgery. Alternatively, the surgery suitability may be output by quantifying or visualizing a degree of suitability for surgery.

The laser surgery availability prediction model may predict whether a vision correction surgery using a laser is available for the subject. Here, the vision correction surgery using the laser may refer to a surgery for correcting a visual ability through conical cutting using the laser. The laser surgery availability prediction model may predict whether a laser surgery is possible based on the input data.

The availability of the vision correction surgery using the laser may refer to medical availability. Accordingly, the input data of the laser surgery availability prediction model may not include the preference of the subject with regard to the vision correction surgery. Alternatively, the laser surgery availability prediction model may predict laser surgery availability without consideration of the preference of the subject with regard to the vision correction surgery.

The laser surgery availability may be output as available/unavailable for laser surgery. Alternatively, the laser surgery availability may be output by quantifying or visualizing a degree of availability for surgery.

The corneal shape factor prediction model may predict a corneal shape factor of the subject after the vision correction surgery. The model may predict one or more corneal shape factors. The corneal shape factor prediction model may predict the corneal shape factors based on input data.

The input data of the corneal shape factor prediction model may include surgery parameters. For example, the input data may include a type of surgery as the surgery parameter. The model may predict a corneal shape factor corresponding to the input surgery parameter. As an example, when the input data includes LASIK, LASEK, and SMILE as the surgery parameter, an output of the model may include a corneal shape factor prediction value after LASIK, a corneal shape factor prediction value after LASEK, and a corneal shape factor prediction value after SMILE. As another example, when the input data includes a standard vision correction surgery and a custom vision correction surgery as the surgery parameter, the output of the model may include a corneal shape factor prediction value after the standard vision correction surgery and a corneal shape factor prediction value after the custom vision correction surgery.

The corneal shape factor prediction model may predict a corneal shape factor corresponding to a predetermined surgery parameter regardless of whether the input data includes the surgery parameter. For example, in the case in which the model is trained to predict the corneal shape factor after the standard vision correction surgery and the corneal shape factor after the custom vision correction surgery, even when the input data of the model excludes the surgery parameter, the model may output the corneal shape factor prediction value after the standard vision correction surgery and the corneal shape factor prediction value after the custom vision correction surgery.

Table 1 shows the outputs of the corneal shape factor prediction model according to an embodiment. Referring to Table 1, the corneal shape factor prediction model may output IHD, ISV, and IVA values of the subject. Further, the corneal shape factor prediction model may include IHD, ISV, and IVA measurements of the subject obtained before the vision correction surgery, predicted IHD, ISV, and IVA values after the standard vision correction surgery, and predicted IHD, ISV, and IVA values after the custom vision correction surgery.

TABLE 1

| Item | Current | Prediction after standard vision correction surgery | Prediction after custom vision correction surgery |
|---|---|---|---|
| IHD | 0.015 | 0.021 | 0.018 |
| ISV | 20.0 | 27.8 | 25.0 |
| IVA | 0.19 | 0.23 | 0.22 |

The custom vision correction surgery necessity prediction model may predict whether the subject needs a custom vision correction surgery. The custom vision correction surgery necessity prediction model may predict the custom vision correction surgery necessity based on input data.

The custom vision correction surgery necessity prediction model may predict the custom vision correction surgery necessity without consideration of the preference of the subject with regard to the vision correction surgery. Alternatively, the custom vision correction surgery necessity prediction model may predict the custom vision correction surgery necessity in consideration of the preference of the subject with regard to the vision correction surgery. An output of the custom vision correction surgery necessity prediction model may vary according to whether the preference of the subject with regard to the vision correction surgery is considered.

The custom vision correction surgery necessity prediction model may determine whether the subject needs the custom vision correction surgery based on eye characteristic data, such as a conical shape factor and a conical topography image.

The custom vision correction surgery necessity prediction model may determine the custom vision correction surgery necessity based on an absolute numerical value of the conical shape factor. For example, when the corneal shape factor is out of a certain range, the custom vision correction surgery necessity prediction model may predict that the subject needs custom vision correction surgery.

The custom vision correction surgery necessity prediction model may determine the custom vision correction surgery necessity based on a relative numerical value of the conical shape factor. For example, the custom vision correction surgery necessity prediction model may compare the corneal shape factor after the standard vision correction surgery with the corneal shape factor after the custom vision correction surgery to determine the custom vision correction surgery necessity.

The vision correction surgery suggestion model may suggest a vision correction surgery corresponding to the subject. As an example, the model may output one vision correction surgery. As another example, the model may output a plurality of vision correction surgeries. As yet another example, the model may output a plurality of vision correction surgeries together with information about their priorities.

The vision correction surgery suggestion model may suggest a vision correction surgery based on input data.

The vision correction surgery corresponding to the subject may refer to a vision correction surgery that is determined by the vision correction surgery suggestion model without consideration of the preference of the subject with regard to the vision correction surgery. Alternatively, the vision correction surgery corresponding to the subject may refer to a vision correction surgery that is determined by the vision correction surgery suggestion model in consideration of the preference of the subject with regard to the vision correction surgery. The output of the vision correction surgery suggestion model may vary according to whether the preference of the subject with regard to the vision correction surgery is considered.

The output of the vision correction surgery suggestion model may be determined in consideration of the custom vision correction surgery necessity. For example, the output may be determined in consideration of the custom vision correction surgery necessity, such as standard LASIK, custom LASIK, standard LASEK, custom LASEK, standard SMILE, custom SMILE, and the like.

Alternatively, the output of the vision correction surgery suggestion model may be determined without consideration of the custom vision correction surgery necessity. For example, the output may be determined without consideration of the custom vision correction surgery necessity, such as LASIK, LASEK, SMILE, lens implantation, and the like.

The vision correction surgery suggestion model may suggest a vision correction surgery based on the quality of vision after the vision correction surgery. For example, the model may suggest a vision correction surgery based on predicted visual ability values after the vision correction surgery, which corresponds to a plurality of vision correction surgeries.

Table 2 shows the outputs of the vision correction surgery suggestion model according to an embodiment. Referring to Table 2, the vision correction surgery suggestion model may output LASIK, LASEK, and SMILE together with information about their priority, such as suitability. In Table 2, a value corresponding to SMILE is greater than values corresponding to LASIK and LASEK, which may mean that the vision correction surgery suggestion model suggests SMILE as a first priority. In addition to the method of Table 2, information about the priority may be output in various ways to indicate the priority.

TABLE 2

| Vision correction surgery type | Suitability |
|---|---|
| LASIK | 15.45% |
| LASER | 13.30% |
| SMILE | 71.25% |

The surgery parameter suggestion model may suggest a surgery parameter. The model may suggest one or more surgery parameters. The surgery parameter suggestion model may suggest the surgery parameters based on input data.

The input data of the surgery parameter suggestion model may include data in the form of an image. Here, the image may be an image obtained through measurement and/or inspection using equipment, such as a corneal topography map. Alternatively, the image may be an image obtained through interpolation, extrapolation, artificial intelligence, or the like based on measured numerical values. For example, the image may be an image generated from the corneal shape factor.

A surgery result after the vision correction surgery performed based on the surgery parameters which are suggested based on images by the surgery parameter suggestion model may be better than a surgery result after the vision correction surgery performed based on the surgery parameters which are suggested based on numerical values. For example, a surgery result after the vision correction surgery performed based on the surgery parameters which are suggested based on the corneal topography image by the model may be better than a surgery result after the vision correction surgery performed based on the surgery parameters which are suggested based on the corneal shape factor, such as IHD, ISV, IVA, or the like. Here, the surgery result may refer to the quality of vision after a surgery. Alternatively, the surgery result may refer to a corneal shape after the surgery.

The visual ability prediction model may predict a visual ability of the subject after the vision correction surgery. The visual ability prediction model may output a predicted visual ability value based on input data. The model may predict one or more visual abilities.

The input data of the visual ability prediction model may include a surgery parameter. For example, the input data may include a type of surgery as the surgery parameter. The model may predict a visual ability corresponding to the input surgery parameter. As an example, when the input data includes LASIK, LASEK, and SMILE as the surgery parameter, an output of the model may include a predicted visual ability value after LASIK, a predicted visual ability value after LASEK, and a predicted visual ability value after SMILE. As another example, when the input data includes a standard vision correction surgery and a custom vision correction surgery as the surgery parameter, the output of the model may include a predicted visual ability value after the standard vision correction surgery and a predicted visual ability value after the custom vision correction surgery.

The visual ability prediction model may predict vision corresponding to a predetermined surgery parameter regardless of whether the input data includes the surgery parameter. For example, in the case in which the model is trained to predict a visual ability after the standard vision correction surgery and a visual ability after the custom vision correction surgery, even when the input data of the model excludes the surgery parameter, the model may output a predicted visual ability value after the standard vision correction surgery and a predicted visual ability value after the custom vision correction surgery.

The visual ability prediction model may predict visual abilities corresponding to a plurality of different time points. For example, the model may predict visual abilities corresponding to a first time and a second time after the vision correction surgery. Examples of the plurality of different time points may include one day, one week, one month, six months, one year, and the like after the vision correction surgery, but not limited thereto.

The visual ability prediction model may predict a visual ability recovery rate of the subject based on the predicted visual ability values corresponding to the plurality of different time points. For example, the model may predict the visual ability recovery rate based on the first time and the second time after the vision correction surgery.

The expected visual ability image generation model may predict a field of view of the subject after the vision correction surgery. The model may generate an image (hereinafter, referred to as an "expected visual ability image") obtained by visualizing the quality of the vision of the subject after the vision correction surgery. The model outputs the expected visual ability image so that it is possible to more easily explain the vision correction surgery to the subject. The model visualizes and outputs the field of view after the vision correction surgery so that the subject may more clearly understand the expected result after the vision correction surgery and, accordingly, may receive aid in selecting the vision correction surgery.

The input data of the expected visual ability image generation model may include a surgery parameter. For example, the input data may include a type of surgery as the surgery parameter. The model may predict an expected visual ability image corresponding to the input surgery parameter. As an example, when the input data includes LASIK, LASEK, and SMILE as the surgery parameter, an output of the model may include an expected visual ability image after LASIK, an expected visual ability image after LASEK, and an expected visual ability image after SMILE. As another example, when the input data includes a standard vision correction surgery and a custom vision correction surgery as the surgery parameter, an output of the model may include an expected visual ability image after the standard vision correction surgery and an expected visual ability image after the custom vision correction surgery. As yet another example, when the input data includes a plurality of optic zones, an output of the model may include a plurality of expected visual ability images corresponding to the plurality of optic zones.

The expected visual ability image generation model may generate an expected visual ability image corresponding to a predetermined surgery parameter regardless of whether the input data includes the surgery parameter. For example, in the case in which the model is trained to generate an expected visual ability image after the standard vision correction surgery and an expected visual ability image after the custom vision correction surgery, even when the input data of the model excludes the surgery parameter, the model may output the expected visual ability image after the standard vision correction surgery and the expected visual ability image after the custom vision correction surgery.

The expected visual ability image may include information about at least one selected from the group of clarity of vision, light bleeding, contrast sensitivity, night vision, glare, double vision, and afterimages of the subject which are expected after the vision correction surgery.

Figure 10:
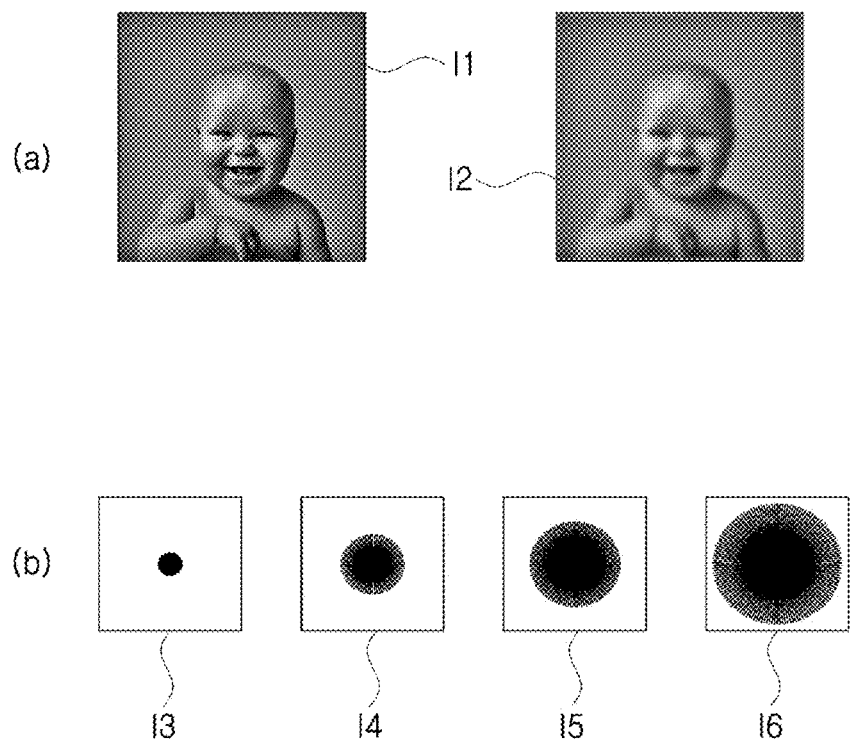
FIG. 10 illustrates views of expected visual ability images according to an embodiment.

FIG. 10 illustrates views of expected visual ability images according to an embodiment. Referring to a of FIG. 10, expected visual ability images I1 and I2 may be expressed by visualizing information about the clarity of vision. Referring to b of FIG. 10, expected visual ability images I3, I4, I5, and I6 may be expressed by visualizing information about light blurring.

A plurality of expected visual ability images may correspond to different surgery parameters. Referring to a of FIG. 10, a first expected visual ability image I1 may correspond to the clarity of vision after a custom vision correction surgery, and a second expected visual ability image I2 may correspond to the clarity of vision after a standard vision correction surgery. Referring to b of FIG. 10, third to sixth expected visual ability images I3 to I6 may be expected visual ability images corresponding to different optic zones. For example, the optic zone of the third expected visual ability image I3 may be greater than the optic zones of the fourth to sixth expected visual ability images I4 to I6.

The expected visual ability images according to an embodiment may be generated by filtering using a filter. Here, the filtering is a concept used in a general image processing field and may refer to generation of a filtered image by convolution of an image and a filter. Examples of the filter may include an average filter, a weighted average filter, a low-pass filter, a Gaussian filter, a median filter, a bilateral filter, a blurring filter, a high-pass filter, an unsharp masking, a high-boost filter, a sharpening filter, and the like, but not limited thereto.

Figure 11:
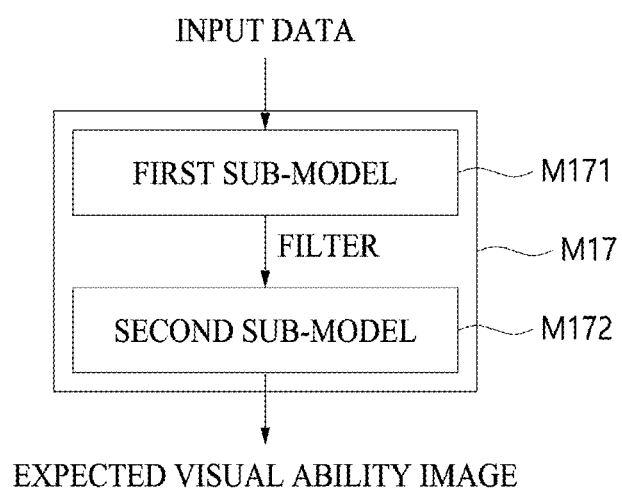
FIG. 11 is a diagram illustrating an expected visual ability image generation model using a filter according to an embodiment.

FIG. 11 is a diagram illustrating an expected visual ability image generation model M17 using a filter according to an embodiment. Referring to FIG. 11, the expected visual ability image generation model M17 may include a first sub-model M171 and a second sub-model M172.

The first sub-model M171 may calculate and/or select a filter based on input data. As an example, the input data may include a prediction value of eye characteristic data of a subject after a vision correction surgery, and the first sub-model M171 may calculate and/or select a filter based on the prediction value of the eye characteristic data. As another example, the input data may include a measurement of the eye characteristic data of the subject and a surgery parameter, and the first sub-model M171 may calculate and/or select a filter based on the measurement of the eye characteristic data and the surgery parameter.

The second sub-model M172 may generate an expected visual ability image based on the filter calculate and/or selected by the first sub-model M171. For example, the second sub-model M172 may generate an expected visual ability image by applying the filter to an original image. Here, the original image is an image that serves as a basis for generating the expected visual ability image and may be input externally from the expected visual ability image generation model M17 or may be included in the model M17.

The corneal topography image prediction model may predict a corneal topography image of the subject after the vision correction surgery. The model may predict one or more corneal topography images. The corneal topography image prediction model may generate a corneal topography image based on input data.

The input data of the corneal topography image prediction model may include a surgery parameter. For example, the input data may include a type of surgery as the surgery parameter. The model may predict a corneal topography image corresponding to the input surgery parameter. As an example, when the input data includes LASIK, LASEK, and SMILE as the surgery parameter, an output of the model may include a corneal topography image after LASIK, a corneal topography image after LASEK, and a corneal topography image after SMILE. As another example, when the input data includes a standard vision correction surgery and a custom vision correction surgery as the surgery parameter, an output of the model may include a corneal topography image after the standard vision correction surgery and a corneal topography image after the custom vision correction surgery.

The corneal topography image prediction model may generate a corneal topography image corresponding to a predetermined surgery parameter regardless of whether the input data includes the surgery parameter. For example, in the case in which the model is trained to generate a corneal topography image after the standard vision correction surgery and a corneal topography image after the custom vision correction surgery, even when the input data of the model excludes the surgery parameter, the model may output the corneal topography image after the standard vision correction surgery and the corneal topography image after the custom vision correction surgery.

Figure 12:
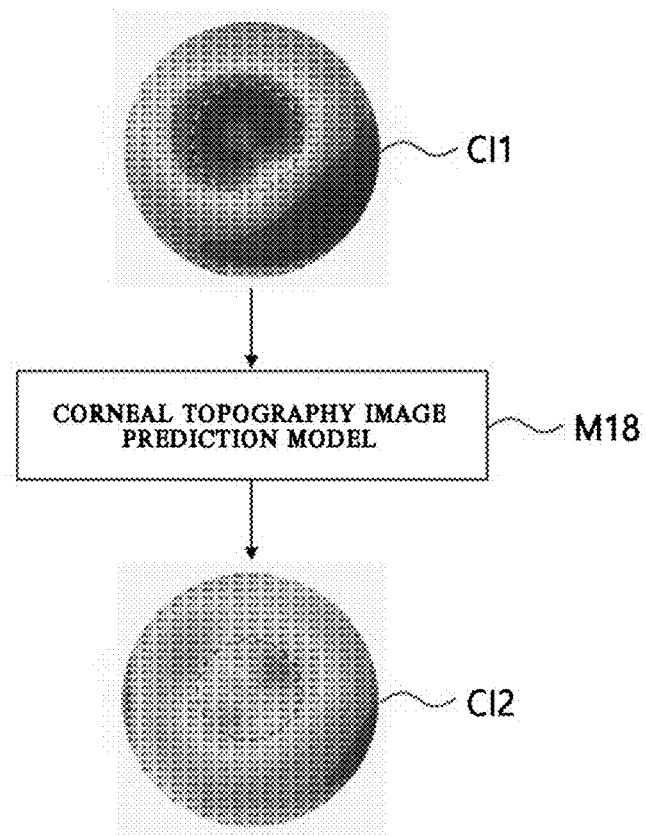
FIG. 12 is a diagram illustrating corneal topography images according to an embodiment.

The input data of the corneal topography image prediction model may include a corneal topography image of the subject measured before the vision correction surgery. FIG. 12 is a diagram illustrating corneal topography images according to an embodiment. Referring to FIG. 12, a corneal topography image prediction model M18 may predict a corneal topography image CI2 of the subject after a vision correction surgery based on a conical topography image CI1 of the subject before the vision correction surgery. In FIG. 12, only the corneal topography image CI1 is illustrated as being input to the model M18, but other pieces of input data may also be input.

The prediction result calculation cause analysis model may analyze a calculation cause for the prediction result generated by the vision correction surgery related model. The model may calculate the dependency of the vision correction surgery related model on the input data. Here, the dependency may include an effect of a specific variable of the input data on the prediction result.

The prediction result calculation cause analysis model may output the calculation cause for the prediction result. The model may output one or more calculation causes for the prediction result. Hereinafter, for convenience of description, the calculation causes for the prediction result are expressed as being numerical values such as dependency coefficients, but the calculation causes for the prediction result are not limited thereto, and there is no limitation on the expression method thereof, such as numerical values, images, text, and combinations thereof. The prediction result calculation cause analysis model may output at least some of the dependency coefficients. For example, the model may output all the calculated dependency coefficients.

The prediction result calculation cause analysis model may output a dependency coefficient that falls within a certain range among the calculated dependency coefficients. For example, the model may output a dependency coefficient greater than a predetermined value among the calculated dependency coefficients. Alternatively, the model may output a dependency coefficient having an absolute value greater than a predetermined value among the calculated dependency coefficients.

The prediction result calculation cause analysis model may output a certain number of dependency coefficients. For example, the model may output a predetermined number of dependency coefficients.

The prediction result calculation cause analysis model may include a surgery suitability prediction analysis model, a laser surgery availability prediction analysis model, a corneal shape factor prediction analysis model, a custom vision correction surgery necessity prediction analysis model, a vision correction surgery suggestion analysis model, a surgery parameter suggestion analysis model, a visual ability prediction analysis model, an expected visual ability image generation analysis model, and a corneal topography image prediction analysis model. For example, the visual ability prediction analysis model may calculate an effect of variables included in the input data of the visual ability prediction model on predicting the visual ability of the visual ability prediction model. Alternatively, the visual ability prediction analysis model may calculate the dependency of the predicted visual ability value calculated by the visual ability prediction model on the input data of the visual ability prediction model.

The prediction result calculation cause analysis model may include at least part of the models of the vision correction surgery related model. For example, the visual ability prediction analysis model may include the visual ability prediction model.

Figure 13:
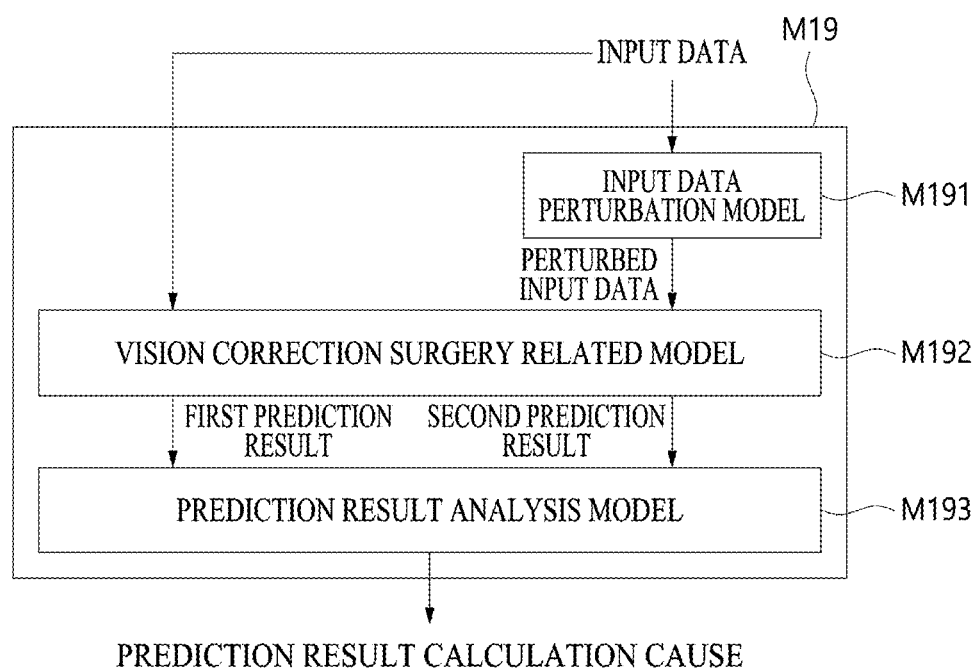
FIG. 13 is a diagram illustrating a prediction result calculation cause analysis model including a vision correction surgery related model according to an embodiment.

FIG. 13 is a diagram illustrating a prediction result calculation cause analysis model M19 including a vision correction surgery related model M192 according to an embodiment. Referring to FIG. 13, the prediction result calculation cause analysis model M19 may include an input data perturbation model M191, a vision correction surgery related model M192, and a prediction result analysis model M193.

The input data perturbation model M191 may output input data perturbed based on input data. The model M191 may output one or more pieces of perturbed input data. Here, the perturbation of the input data may refer to changing of the input data, such as changing of at least part of variables included in the input data. For example, when the variable is a numerical value, the perturbation may refer to increasing or decreasing of the value. Alternatively, when the variable is an image, the perturbation may refer to increasing or decreasing of pixel values of at least part of pixels of the image.

The vision correction surgery related model M192 may output a first prediction result corresponding to the input data and a second prediction result corresponding to the perturbed input data based on the input data and the perturbed input data. For example, when the vision correction surgery related model M192 included in the prediction result calculation cause analysis model M19 is a visual ability prediction model, the first prediction result and the second prediction result may be different predicted visual ability values. Further, when the perturbed input data is provided with a plurality of pieces of perturbed input data, the model may output a plurality of prediction results corresponding to the plurality of pieces of perturbed input data.

The prediction result analysis model M193 may output calculation causes for the prediction results based on the prediction results. For example, the model M193 may calculate the calculation causes for the prediction results based on the first prediction result calculated from the unperturbed input data and the second prediction result calculated from the perturbed input data. Specifically, the dependency of the first prediction result on a first variable may be calculated based on a difference between the first prediction result and the second prediction result calculated from the input data in which the first variable is perturbed.

Figure 14:
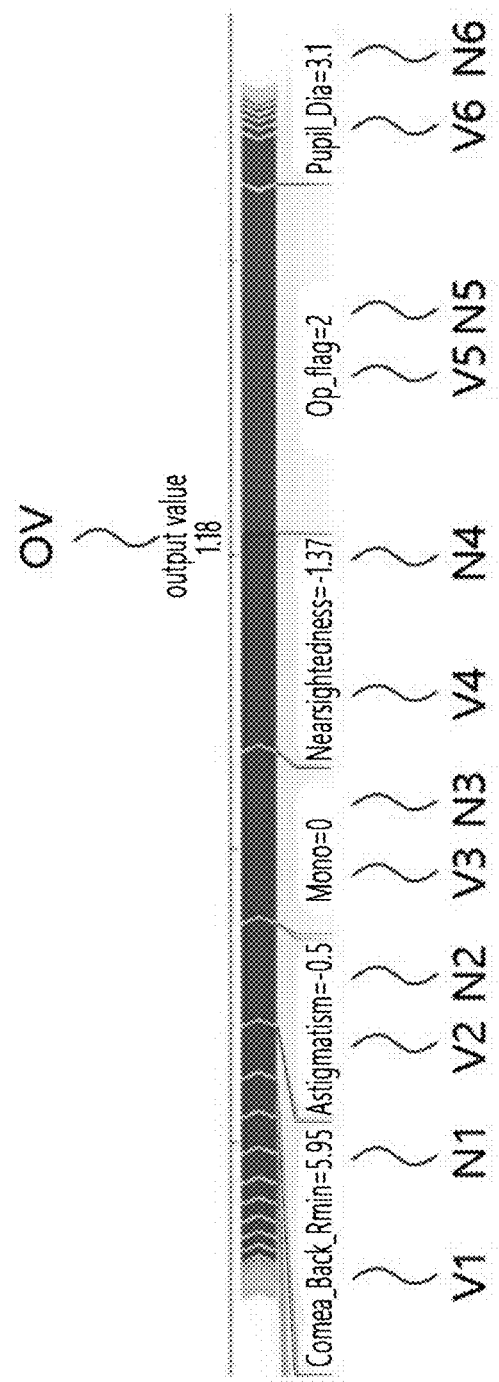
FIG. 14 is a view illustrating a calculation cause for a prediction result according to an embodiment calculation.

FIG. 14 is a view illustrating a calculation cause for a prediction result according to an embodiment calculation and, specifically, is a view illustrating a cause for visual ability prediction. Referring to FIG. 14, the calculation cause for the prediction result may be expressed as a numerical value and an image. Characters such as Cornea_Back_Rmin V1, Astigmatism V2, Mono V3, Nearsightedness V4, Op_flag V5, and Pupil_Dia V6 illustrated in FIG. 14 may correspond to variables included in input data. 5.95 N1, −0.5 N2, 0 N3, −1.37 N4, 2 N5, and 3.1 N6 expressed to correspond to the characters may correspond to numerical values of the variables included in the input data.

The dependency of the prediction result on the variables may be visualized and expressed. For example, the dependency may be expressed by a length, color, and direction of an arrow. Referring to FIG. 14, the length of the arrow may correspond to an absolute value of a dependency coefficient. Further, the direction and color of the arrow may correspond to a sign of the dependency coefficient. In FIG. 14, it may be interpreted that a predicted visual ability value OV is 1.18, Cornea_Back_Rmin V1, Astigmatism V2, Mono V3, and Nearsightedness V4 have a positive effect on the predicted visual ability value, and Op_flag V5 and Pupil_Dia V6 have a negative effect on the predicted visual ability value.

Examples of the prediction result calculation cause analysis model may include local interpretable model-agnostic explanations (LIME) and the like, but not limited thereto.

The vision correction surgery related models may be combined with each other. The models may be combined in at least one of a serial connection manner or a parallel connection manner.

The vision correction surgery related models connected in series may mean that an output of at least one vision correction surgery related model is calculated based on an output of at least another vision correction surgery related model.

The vision correction surgery related models connected in parallel may mean that an output of one vision correction surgery related model does not affect an output of another vision correction surgery related model.

Hereinafter, examples of a combination of the vision correction surgery related models will be described.

Figure 15:
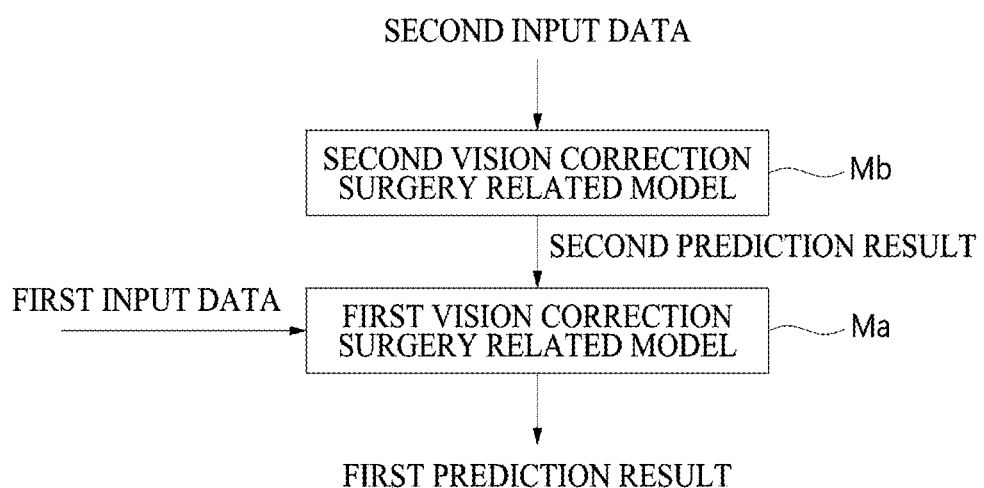
FIG. 15 is a diagram illustrating vision correction surgery related models connected in series according to an embodiment.

FIG. 15 is a diagram illustrating vision correction surgery related models connected in series according to an embodiment. Referring to FIG. 15, a first vision correction surgery related model Ma and a second vision correction surgery related model Mb may be combined in a serial connection manner. The first vision correction surgery related model Ma may calculate a first prediction result based on first input data and a second prediction result which is output by the second vision correction surgery related model Mb receiving second input data.

FIGS. 16 to 19 are diagrams illustrating calculation of outputs of vision correction surgery related models based on an output of a corneal shape factor prediction model according to an embodiment.

Figure 16:
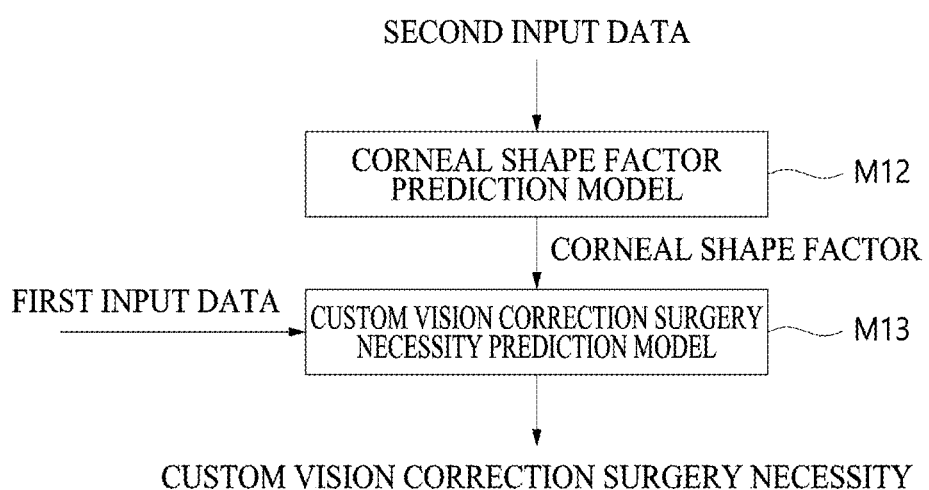
FIGS. 16 to 19 are diagrams illustrating calculation of outputs of vision correction surgery related models based on an output of a corneal shape factor prediction model according to an embodiment.

Referring to FIG. 16, a custom vision correction surgery necessity prediction model M13 may predict a custom vision correction surgery necessity of a subject based on a corneal shape factor which is outputted by a corneal shape factor prediction model M12 receiving second input data and first input data.

Figure 17:
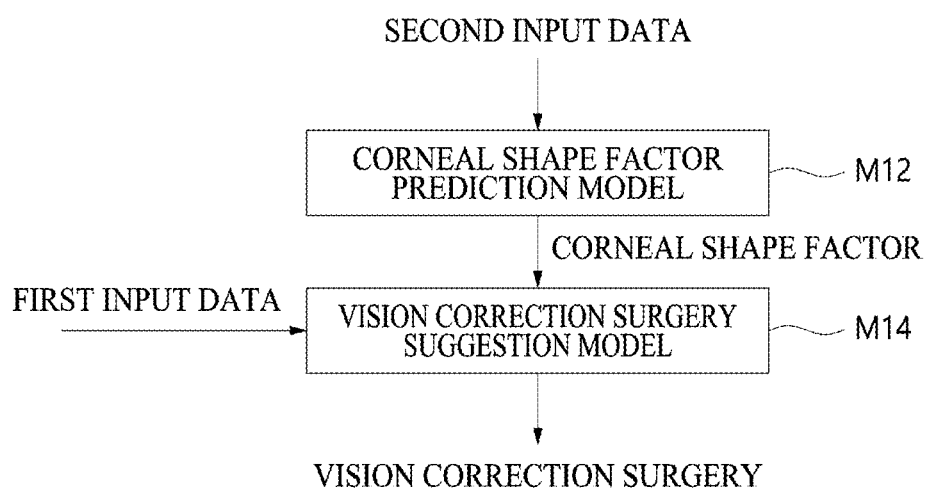

Referring to FIG. 17, a vision correction surgery suggestion model M14 may suggest a vision correction surgery corresponding to the subject based on a corneal shape factor which is outputted by a corneal shape factor prediction model M12 receiving second input data and first input data.

Figure 18:
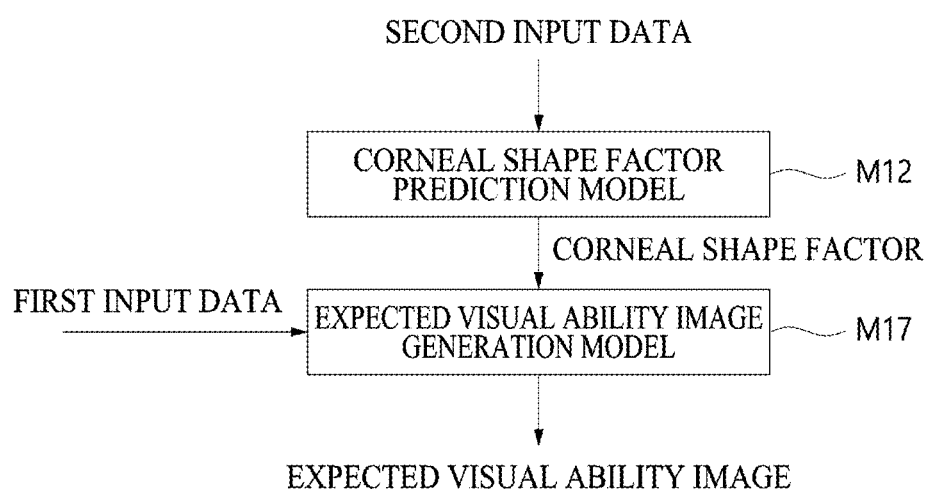

Referring to FIG. 18, an expected visual ability image generation model M17 may generate an expected visual ability image of a subject after a vision correction surgery based on a corneal shape factor which is outputted by a corneal shape factor prediction model M12 receiving second input data and first input data.

Figure 19:
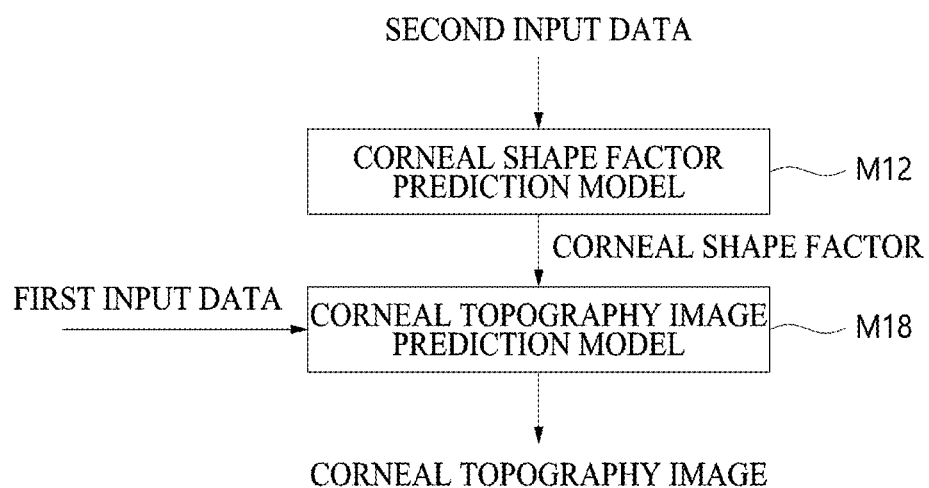

Referring to FIG. 19, a corneal topography image prediction model M18 may predict a corneal topography image of a subject after a vision correction surgery based on a corneal shape factor which is outputted by a corneal shape factor prediction model M12 receiving second input data and first input data.

Figure 20:
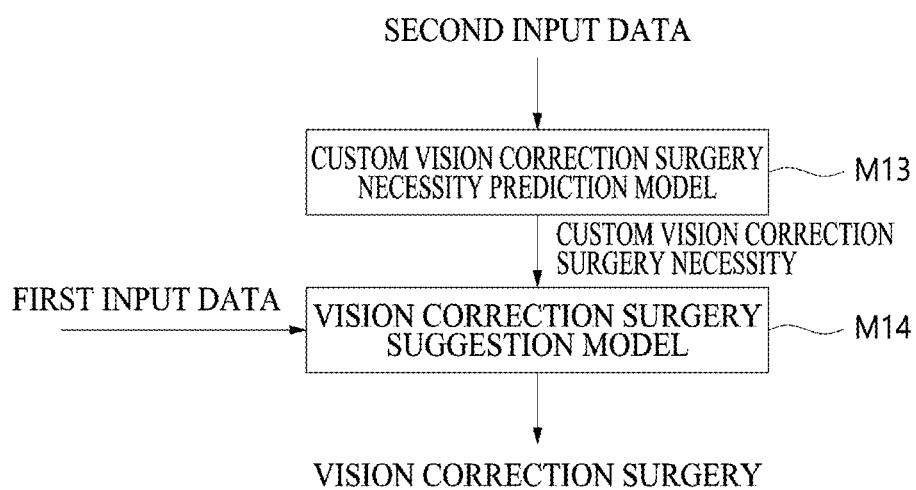
FIG. 20 is a diagram illustrating calculation of an output of a vision correction surgery related model based on an output of a custom vision correction surgery necessity prediction model according to an embodiment.

FIG. 20 is a diagram illustrating calculation of an output of a vision correction surgery related model based on an output of a custom vision correction surgery necessity prediction model according to an embodiment. Referring to FIG. 20, a vision correction surgery suggestion model M14 may suggest a vision correction surgery corresponding to a subject based on a custom vision correction surgery necessity which is outputted by a custom vision correction surgery necessity prediction model M13 receiving second input data and first input data.

Figure 21:
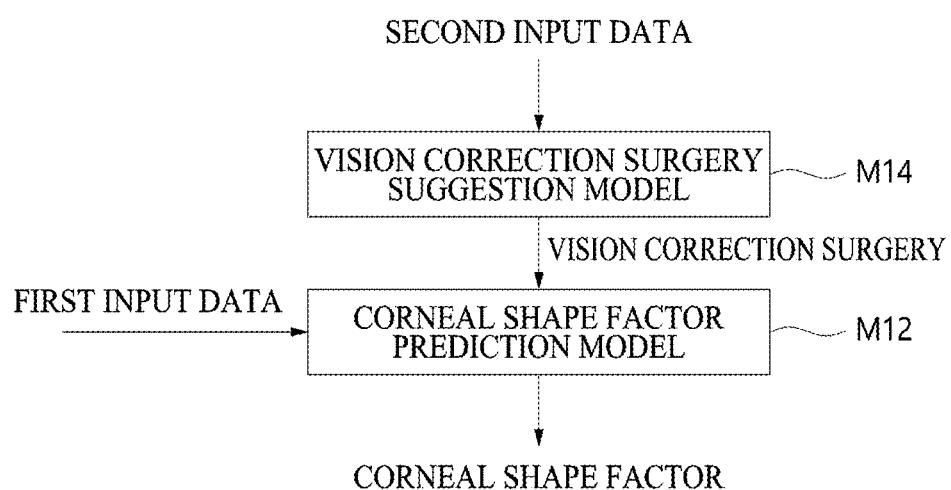
FIGS. 21 and 22 are diagrams illustrating calculation of outputs of vision correction surgery related models based on an output of a vision correction surgery suggestion model according to an embodiment.
Figure 22:
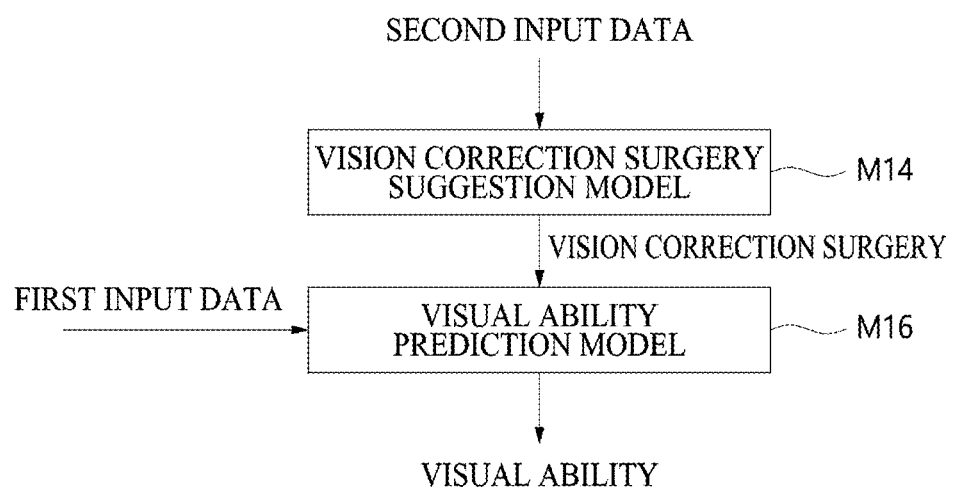

FIGS. 21 and 22 are diagrams illustrating calculation of outputs of vision correction surgery related models based on an output of a vision correction surgery suggestion model according to an embodiment.

Referring to FIG. 21, a corneal shape factor prediction model M12 may predict a corneal shape factor of a subject after a vision correction surgery based on a vision correction surgery which is outputted by a vision correction surgery suggestion model M14 receiving second input data and first input data.

Referring to FIG. 22, a visual ability prediction model M16 may calculate a predicted visual ability value of a subject after a vision correction surgery based on a vision correction surgery which is outputted by a vision correction surgery suggestion model M14 receiving second input data and first input data.

An expected visual ability image generation model may generate an expected visual ability image of a subject after a vision correction surgery based on a vision correction surgery which is outputted by a vision correction surgery suggestion model receiving second input data and first input data.

A corneal topography image prediction model may predict a corneal topography image of a subject after a vision correction surgery based on a vision correction surgery which is outputted by a vision correction surgery suggestion model receiving second input data and first input data.

Figure 23:
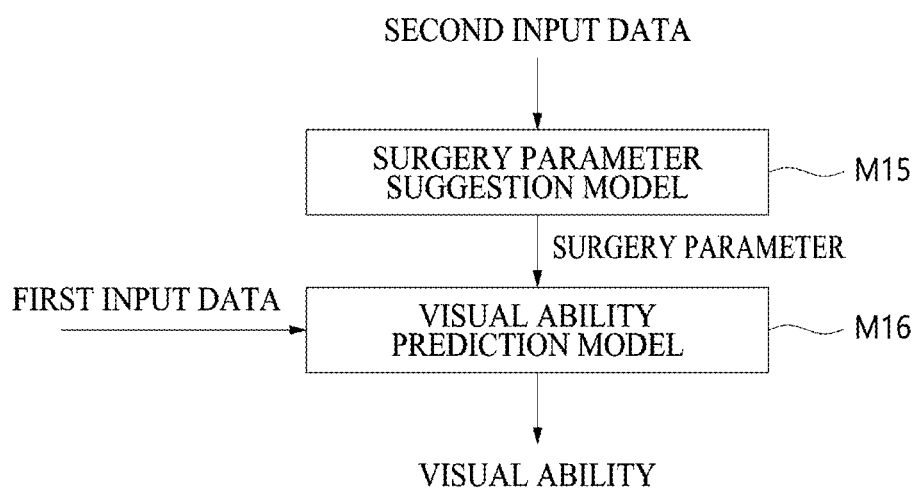
FIG. 23 is a diagram illustrating calculation of an output of the vision correction surgery related model based on an output of a surgery parameter suggestion model according to an embodiment.

FIG. 23 is a diagram illustrating calculation of an output of a vision correction surgery related model based on an output of a surgery parameter suggestion model according to an embodiment.

Referring to FIG. 23, a visual ability prediction model M16 may calculate a predicted visual ability value of the subject after a vision correction surgery based on a surgery parameter which is output by a surgery parameter suggestion model M15 receiving second input data and first input data.

A corneal shape factor prediction model may predict a corneal shape factor of a subject after a vision correction surgery based on a surgery parameter which is output by a surgery parameter suggestion model receiving second input data and first input data.

An expected visual ability image generation model may generate an expected visual ability image of a subject after a vision correction surgery based on a surgery parameter which is outputted by a surgery parameter suggestion model receiving second input data and first input data.

A corneal topography image prediction model may predict a corneal topography image of a subject after a vision correction surgery based on a surgery parameter which is output by a surgery parameter suggestion model receiving second input data and first input data.

Figure 24:
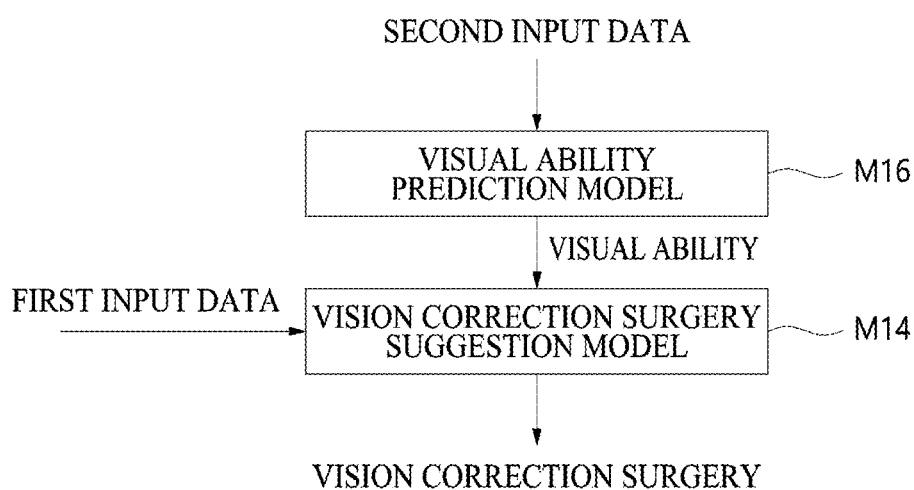
FIGS. 24 and 25 are diagrams illustrating calculation of outputs of vision correction surgery related models based on an output of a visual ability prediction model according to an embodiment.
Figure 25:
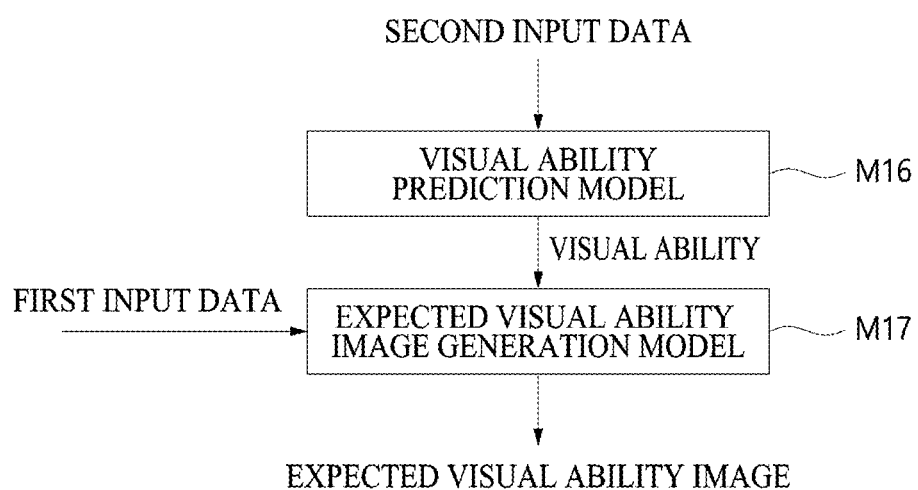

FIGS. 24 and 25 are diagrams illustrating calculation of outputs of vision correction surgery related models based on an output of a visual ability prediction model according to an embodiment.

Referring to FIG. 24, a vision correction surgery suggestion model M14 may suggest a vision correction surgery corresponding to a subject based on a predicted visual ability value which is output by the visual ability prediction model M16 receiving second input data and first input data.

Referring to FIG. 25, an expected visual ability image generation model M17 may generate an expected visual ability image of a subject after a vision correction surgery based on a predicted visual ability value which is output by a visual ability prediction model M16 receiving second input data and first input data.

Figure 26:
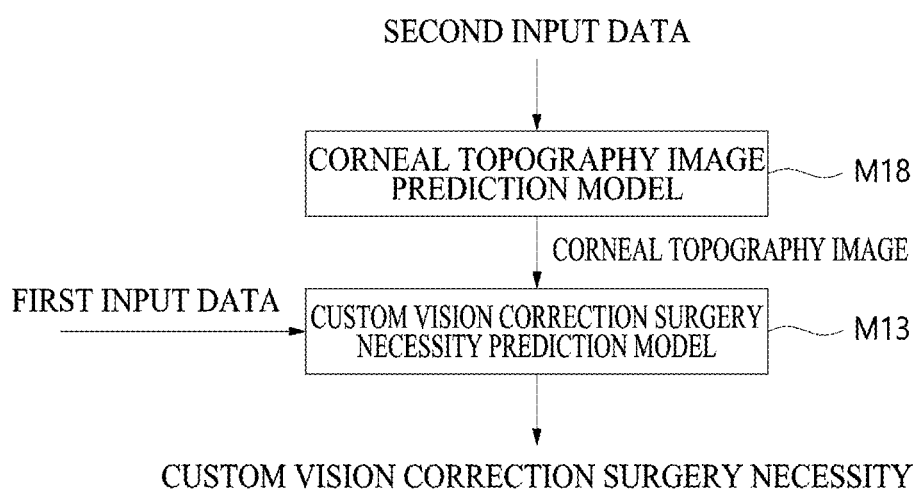
FIGS. 26 and 27 are diagrams illustrating calculation of outputs of vision correction surgery related models based on an output of a corneal topography image prediction model according to an embodiment.
Figure 27:
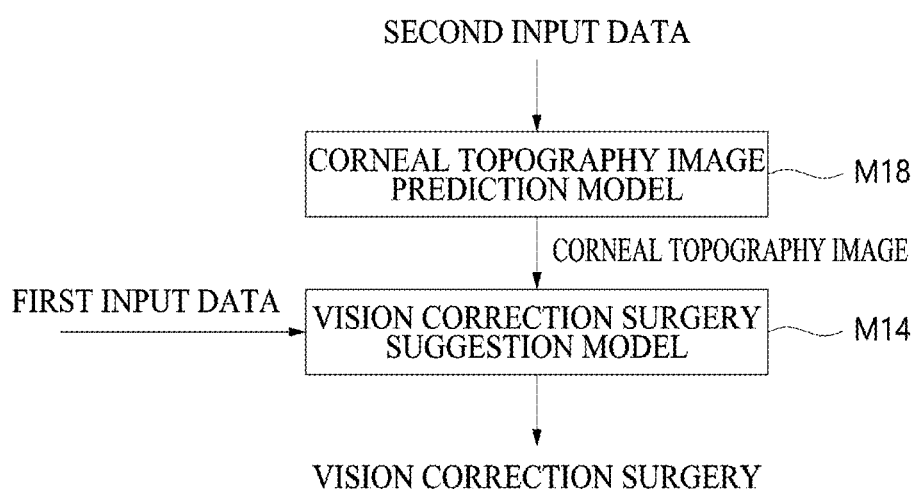

FIGS. 26 and 27 are diagrams illustrating calculation of outputs of vision correction surgery related models based on an output of a corneal topography image prediction model according to an embodiment.

Referring to FIG. 26, a custom vision correction surgery necessity prediction model M13 may predict a custom vision correction surgery necessity of a subject based on a corneal topography image which is output by a corneal topography image prediction model M18 receiving second input data and first input data.

Referring to FIG. 27, a vision correction surgery suggestion model M14 may suggest a vision correction surgery corresponding to a subject based on a corneal topography image which is output by a corneal topography image prediction model M18 receiving second input data and first input data.

A corneal shape factor prediction model may predict a corneal shape factor of a subject after a vision correction surgery based on a corneal topography image which is output by a corneal topography image prediction model receiving second input data and first input data.

An expected visual ability image generation model may generate an expected visual ability image of a subject after a vision correction surgery based on a corneal topography image which is output by a corneal topography image prediction model receiving second input data and first input data.

Figure 28:
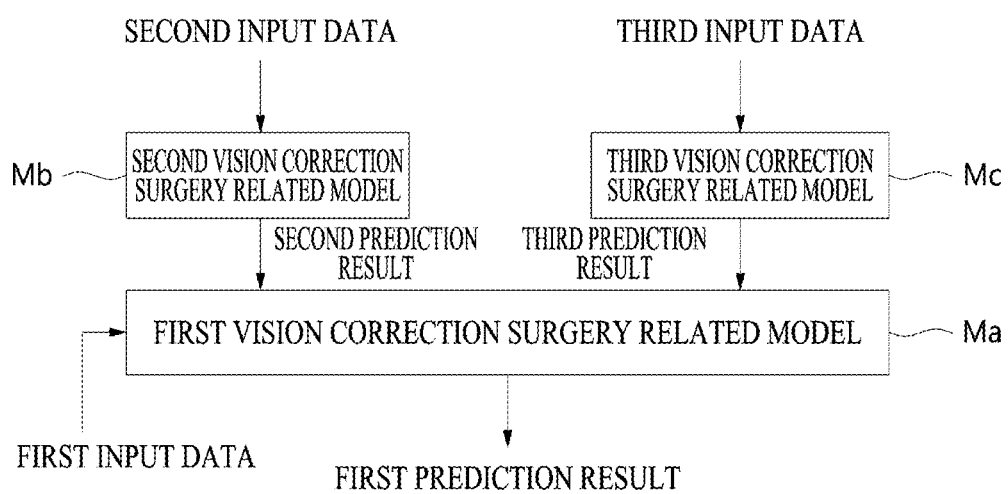
FIG. 28 is a diagram for describing a combination of three or more vision correction surgery related models according to an embodiment.

Three or more vision correction surgery related models may be combined in series and/or in parallel. FIG. 28 is a diagram for describing a combination of three or more vision correction surgery related models according to an embodiment. Referring to FIG. 28, a first vision correction surgery related model Ma may calculate a first prediction result by inputting a second prediction result which is output by a second vision correction surgery related model Mb receiving second input data, a third prediction result which is output by a third vision correction surgery related model Mc receiving third input data, and first input data. Here, the first vision correction surgery related model Ma may be regarded as being connected to the second vision correction surgery related model Mb and the third vision correction surgery related model Mc in series. Further, the second vision correction surgery related model Mb and the third vision correction surgery related model Mc may be regarded as being connected to each other in parallel.

Figure 29:
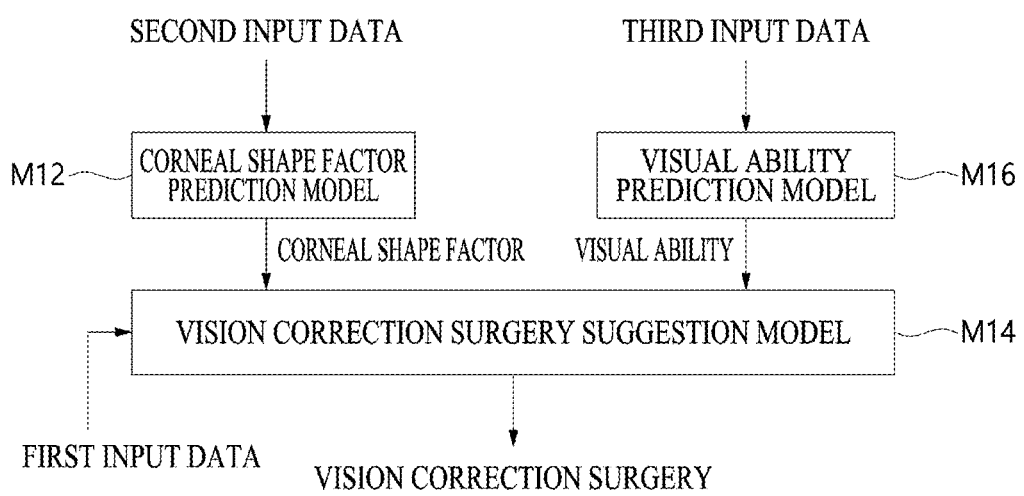
FIGS. 29 and 30 are diagrams illustrating calculation of outputs of vision correction surgery related models based on outputs of a conical shape factor prediction model and a visual ability prediction model according to an embodiment.
Figure 30:
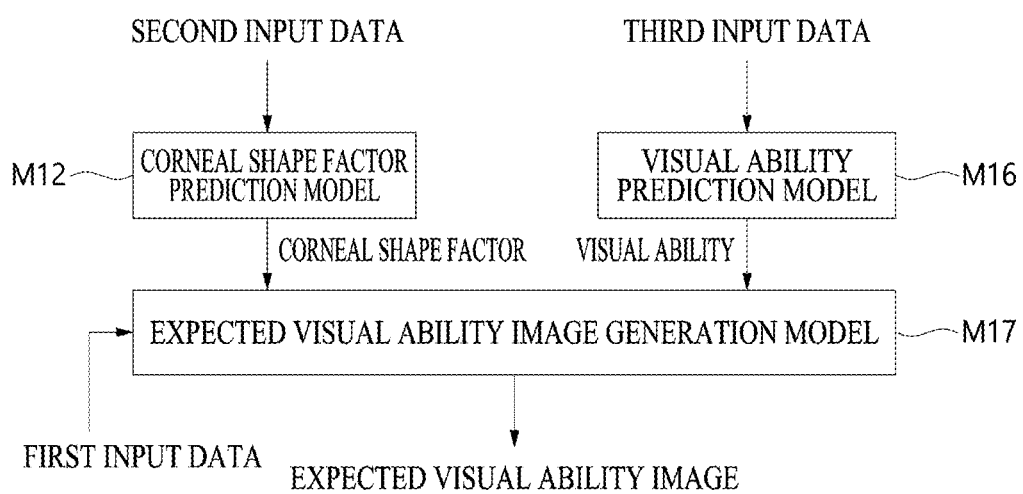

FIGS. 29 and 30 are diagrams illustrating calculation of outputs of vision correction surgery related models based on outputs of a corneal shape factor prediction model and a visual ability prediction model according to an embodiment.

Referring to FIG. 29, a vision correction surgery suggestion model M14 may suggest a vision correction surgery corresponding to a subject based on a corneal shape factor which is output by a corneal shape factor prediction model M12 receiving second input data, a predicted visual ability value which is output by a visual ability prediction model M16 receiving third input data, and first input data.

Referring to FIG. 30, an expected visual ability image generation model M17 may generate an expected visual ability image of a subject after a vision correction surgery based on a corneal shape factor which is output by a corneal shape factor prediction model M12 receiving second input data, a predicted visual ability value which is output by a visual ability prediction model M16 receiving third input data, and first input data.

The vision correction surgery related models may be merged with each other. A plurality of vision correction surgery related models may be merged into one model to execute at least part of functions of the plurality of individual models.

Figure 31:
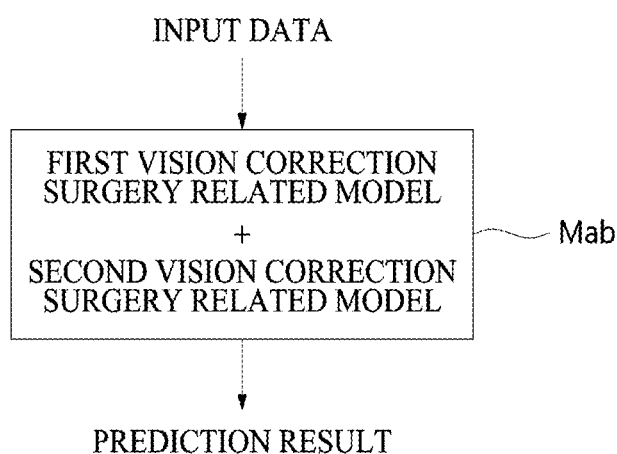
FIG. 31 is a diagram for describing a merging of vision correction surgery related models according to an embodiment.

FIG. 31 is a diagram for describing a merging of vision correction surgery related models according to an embodiment. Referring to FIG. 31, a first vision correction surgery related model and a second vision correction surgery related model may be merged to form one model Mab. The one model Mab may calculate a prediction result based on input data. Here, the prediction result may include information corresponding to at least one of a first prediction result corresponding to an output of the first vision correction surgery related model or a second prediction result corresponding to an output of the second vision correction surgery related model. For example, the prediction result may include at least one of the first prediction result or the second prediction result. Alternatively, the prediction result may include information about at least one of the first prediction result or the second prediction result.

In FIG. 31, the case in which two models are merged is described, but not limited thereto, and three or more models may be merged.

Figure 32:
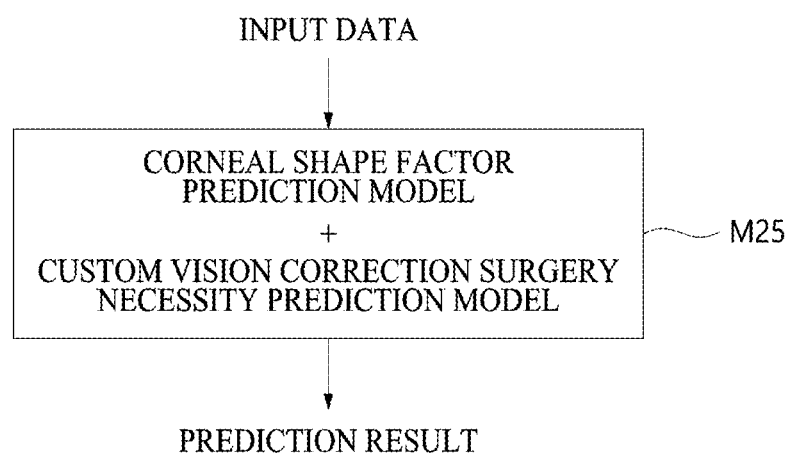
FIGS. 32 to 34 are diagrams illustrating implementation examples of a merging of vision correction surgery related models according to an embodiment.
Figure 33:
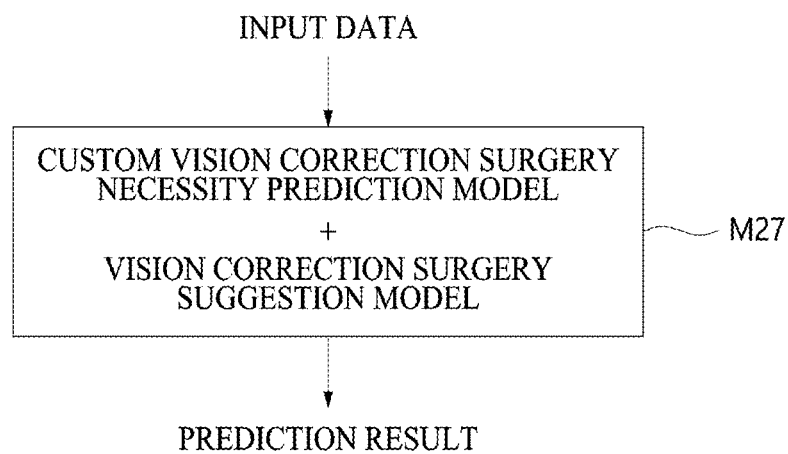
Figure 34:
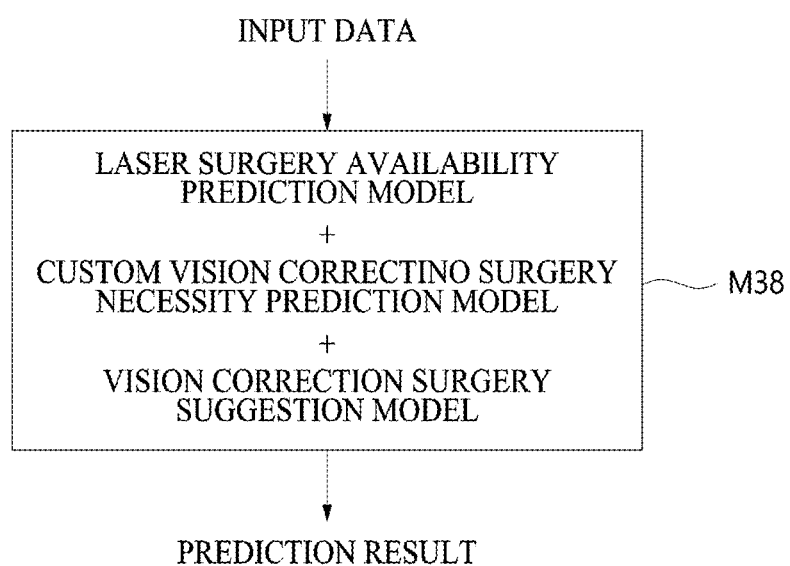

FIGS. 32 to 34 are diagrams illustrating implementation examples of a merging of vision correction surgery related models according to an embodiment.

Referring to FIG. 32, a corneal shape factor prediction model and a custom vision correction surgery necessity prediction model may be merged. The merged model M25 may calculate a prediction result based on input data. The prediction result may include information corresponding to at least one of a corneal shape factor or a custom vision correction surgery necessity. For example, the prediction result may include at least one of the corneal shape factor or the custom vision correction surgery necessity.

Referring to FIG. 33, a custom vision correction surgery necessity prediction model and a vision correction surgery suggestion model may be merged. The merged model M27 may calculate a prediction result based on input data. The prediction result may include information corresponding to at least one of a custom vision correction surgery necessity or a vision correction surgery. For example, the prediction result may include at least one of the custom vision correction surgery necessity or the vision correction surgery.

Referring to FIG. 34, a laser surgery availability prediction model, a custom vision correction surgery necessity prediction model, and a vision correction surgery suggestion model may be merged. The merged model M38 may calculate a prediction result based on input data. The prediction result may include information corresponding to at least one selected from the group of a laser surgery availability, a custom vision correction surgery necessity, and a vision correction surgery. For example, the prediction result may include at least one selected from the group of the laser surgery availability, the custom vision correction surgery necessity, and the vision correction surgery.

Hereinafter, examples of a method of recommending a vision correction surgery will be described.

The method of recommending the vision correction surgery may be implemented using one or more vision correction surgery related models. When the method is implemented using a plurality of vision correction surgery related models, whether to execute at least one vision correction surgery related model may depend on a prediction result of at least another vision correction surgery related model. For example, whether to execute a second vision correction surgery related model may depend on a prediction result of a first vision correction surgery related model.

Operations of a method of recommending a vision correction surgery which will be described below may be performed by a prediction device.

Figure 35:
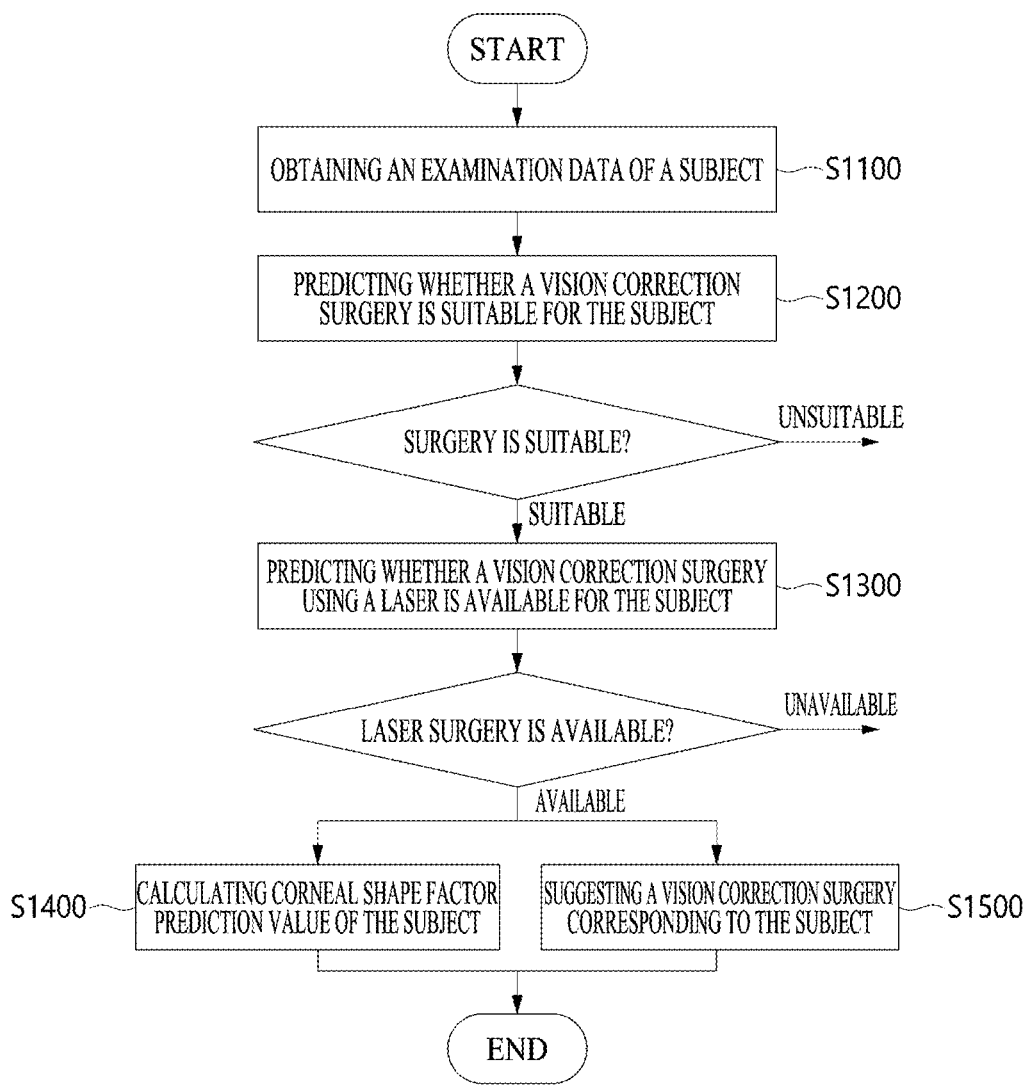
FIG. 35 is a diagram illustrating a first example of a method of recommending a vision correction surgery according to an embodiment.

FIG. 35 is a diagram illustrating a first example of a method of recommending a vision correction surgery according to an embodiment.

Referring to FIG. 35, the method of recommending the vision correction surgery according to an embodiment may include an operation S1100 of obtaining examination data of a subject, an operation S1200 of predicting whether a vision correction surgery is suitable for the subject, an operation S1300 of predicting whether a vision correction surgery using a laser is available for the subject, an operation S1400 of calculating a corneal shape factor prediction value of the subject, and an operation S1500 of suggesting a vision correction surgery corresponding to the subject.

The operation S1100 of obtaining the examination data of the subject may include obtaining, by a computing device, the examination data including interview data and a measurement of eye characteristic data.

The operation S1200 of predicting whether the vision correction surgery is suitable for the subject may include predicting whether the vision correction surgery is suitable for the subject by inputting first group data obtained from the examination data of the subject to a first prediction model. The first prediction model may be a surgery suitability prediction model. The surgery suitability prediction model may predict whether the vision correction surgery is suitable for the subject based on the first group data.

The operation S1300 of predicting whether the vision correction surgery using the laser is available for the subject may include predicting whether the vision correction surgery using the laser is available for the subject by inputting second group data obtained from the examination data of the subject to a second prediction model. Whether to perform the operation S1300 may depend on whether the vision correction surgery is suitable for the subject. For example, the operation S1300 may be performed when the vision correction surgery is suitable for the subject. The second prediction model may be a laser surgery availability prediction model. The laser surgery availability prediction model may predict a laser surgery availability for the subject based on the second group data.

The operation S1400 of calculating the corneal shape factor prediction value of the subject may include calculating a corneal shape factor prediction value of the subject after a standard vision correction surgery and a corneal shape factor prediction value of the subject after a custom vision correction surgery by inputting third group data obtained from the examination data of the subject to a third prediction model. Whether to perform the operation S1400 may depend on whether the vision correction surgery using the laser is available for the subject. For example, the operation S1400 may be performed when the vision correction surgery using the laser is available for the subject. The third prediction model may be a corneal shape factor prediction model. The third prediction model may predict the corneal shape factor based on the third group data. In this case, a custom vision correction surgery necessity may be determined based on the corneal shape factor.

The operation S1500 of suggesting the vision correction surgery corresponding to the subject may include suggesting the vision correction surgery corresponding to the subject by inputting fourth group data obtained from the examination data of the subject to a fourth prediction model. Whether to perform the operation S1500 may depend on whether the vision correction surgery using the laser is available for the subject. For example, the operation S1500 may be performed when the vision correction surgery using the laser is available for the subject. The fourth prediction model may be trained based on at least one selected from the group of examination data of a plurality of patients who have undergone vision correction surgeries, vision correction surgeries corresponding to the plurality of patients, and visual abilities of the plurality of patients after the vision correction surgeries. The fourth prediction model may be a vision correction surgery suggestion model. The fourth prediction model may suggest the vision correction surgery corresponding to the subject based on the fourth group data.

Referring to FIG. 35, the vision correction surgery may be a surgery determined without consideration of the corneal shape factor prediction value and/or the custom vision correction surgery necessity. For example, the vision correction surgery may include LASIK, LASEK, and SMILE. Further, since lens implantation is not unavailable even when a laser vision correction surgery is available, the vision correction surgery may include lens implantation, which is the same in other examples and implementation examples of the present specification. In this case, the vision correction surgery in which the corneal shape factor prediction value and/or the custom vision correction surgery necessity are considered may be determined by a doctor and/or a counselor. For example, the doctor and/or the counselor may determine a vision correction surgery in consideration of a necessity of a custom vision correction surgery, such as standard LASIK, standard LASEK, standard SMILE, custom LASIK, custom LASEK, custom SMILE, and the like, based on the conical shape factor prediction value and the vision correction surgery which are output by the method of recommending the vision correction surgery of FIG. 35.

Figure 36:
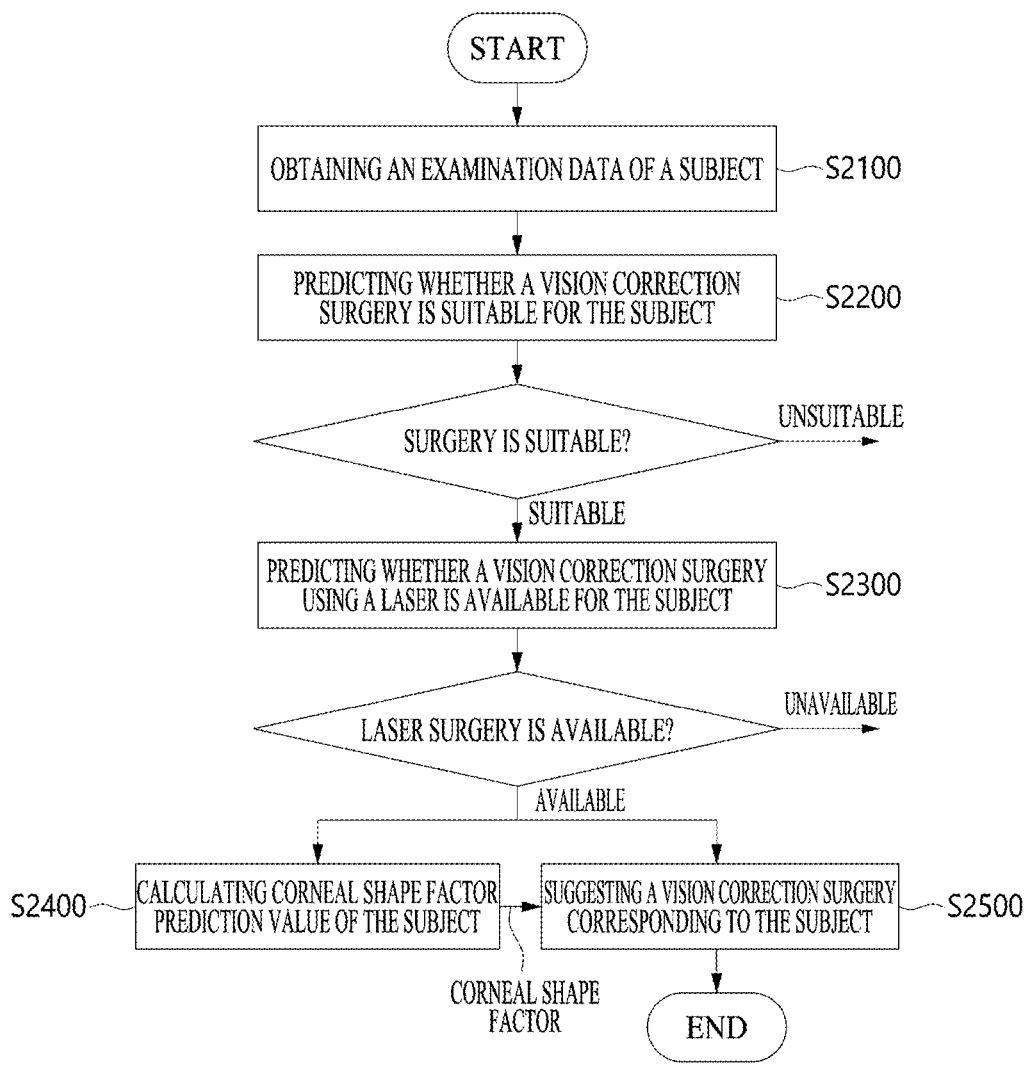
FIG. 36 is a diagram illustrating a second example of the method of recommending the vision correction surgery according to an embodiment.

FIG. 36 is a diagram illustrating a second example of the method of recommending the vision correction surgery according to an embodiment.

Referring to FIG. 36, the method of recommending the vision correction surgery according to an embodiment may include an operation S2100 of obtaining examination data of a subject, an operation S2200 of predicting whether a vision correction surgery is suitable for the subject, an operation S2300 of predicting whether a vision correction surgery using a laser is available for the subject, an operation S2400 of calculating a corneal shape factor prediction value of the subject, and an operation S2500 of suggesting a vision correction surgery corresponding to the subject.

Since the method of recommending the vision correction surgery of FIG. 36 is similar to that of FIG. 35, differences from FIG. 35 will be mainly described.

Referring to FIG. 36, in the operation S2500 of suggesting the vision correction surgery corresponding to the subject, a vision correction surgery may be suggested based on a corneal shape factor prediction value after a standard vision correction surgery and a corneal shape factor prediction value after a custom vision correction surgery which are calculated in the operation of calculating the corneal shape factor prediction value of the subject. The vision correction surgery may be a surgery determined in consideration of a custom vision correction surgery necessity. For example, the vision correction surgery may include standard LASIK, standard LASEK, standard SMILE, custom LASIK, custom LASEK, and custom SMILE. Further, the vision correction surgery may include lens implantation.

Figure 37:
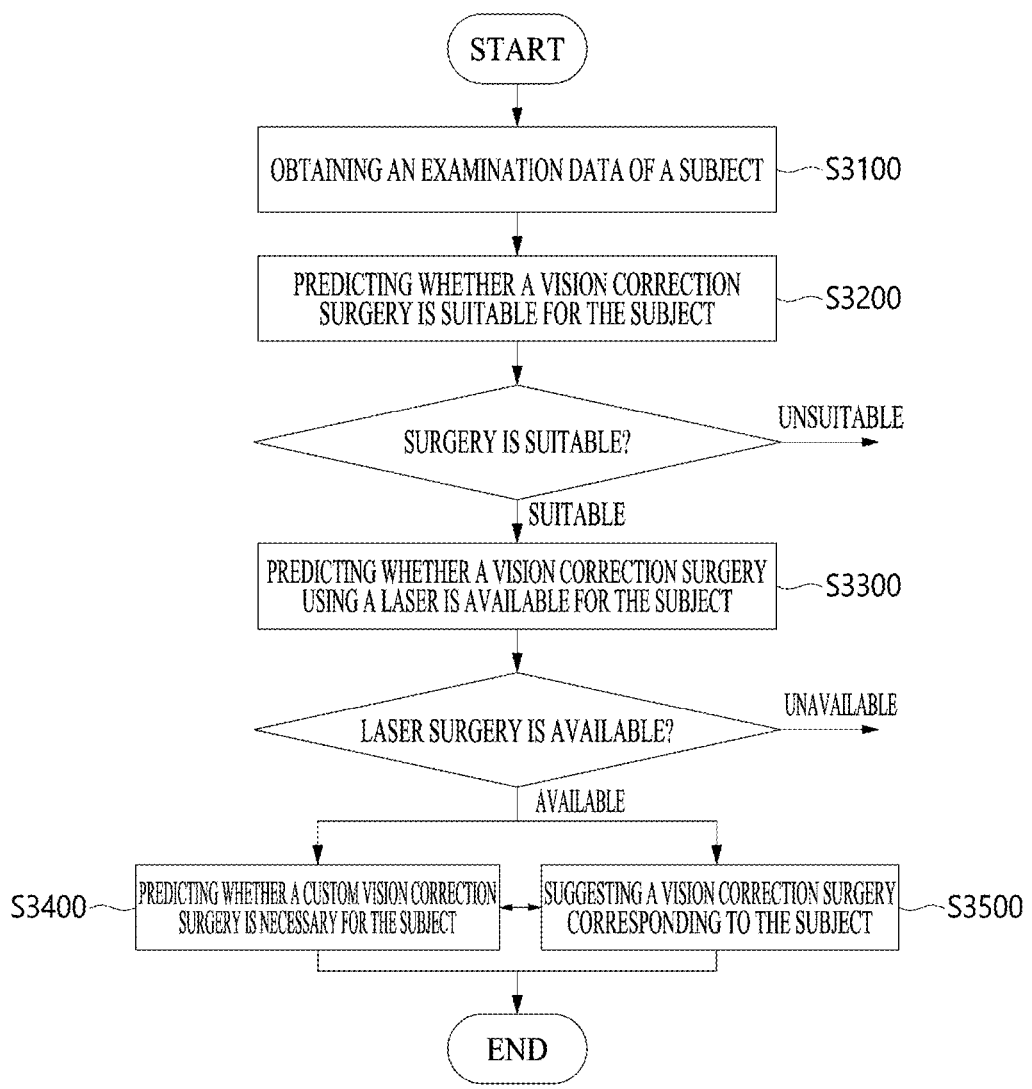
FIG. 37 is a diagram illustrating a third example of the method of recommending the vision correction surgery according to an embodiment.

FIG. 37 is a diagram illustrating a third example of the method of recommending the vision correction surgery according to an embodiment.

Referring to FIG. 37, the method of recommending the vision correction surgery according to an embodiment may include an operation S3100 of obtaining examination data of a subject, an operation S3200 of predicting whether a vision correction surgery is suitable for the subject, an operation S3300 of predicting whether a vision correction surgery using a laser is available for the subject, an operation S3400 of predicting whether the subject needs a custom vision correction surgery, and an operation S3500 of suggesting a vision correction surgery corresponding to the subject.

Since the method of recommending the vision correction surgery of FIG. 37 is similar to that of FIG. 35, differences from FIG. 35 will be mainly described.

Referring to FIG. 37, the operation S3400 of predicting whether the subject needs the custom vision correction surgery may include predicting whether the subject needs the custom vision correction surgery by inputting third group data obtained from the examination data of the subject to a third prediction model. Whether to perform the operation S3400 may depend on whether the vision correction surgery using the laser is available for the subject. For example, the operation S3400 may be performed when the vision correction surgery using the laser is available for the subject. The third prediction model may be a custom vision correction surgery necessity prediction model. The third prediction model may predict the custom vision correction surgery necessity based on the third group data. In the operation, a custom vision correction surgery necessity may be predicted based on a corneal shape factor prediction value of the subject after a standard vision correction surgery and a corneal shape factor prediction value of the subject after a custom vision correction surgery.

The operation S3400 of predicting whether the subject needs the custom vision correction surgery and the operation S3500 of suggesting the vision correction surgery corresponding to the subject may be connected. For example, an output of the operation S3500 of suggesting the vision correction surgery corresponding to the subject may be calculated based on an output of the operation S3400 of predicting whether the subject needs custom vision correction surgery. Alternatively, the output of the operation S3400 of predicting whether the subject needs custom vision correction surgery may be calculated based on an output of the operation S3500 of suggesting the vision correction surgery corresponding to the subject.

As an example, in the operation S3500 of suggesting the vision correction surgery corresponding to the subject, a vision correction surgery may be suggested based on the custom vision correction surgery necessity determined in the operation S3400 of predicting whether the subject needs custom vision correction surgery. For example, the vision correction surgery may include standard LASIK, standard LASEK, standard SMILE, custom LASIK, custom LASEK, and custom SMILE. Further, the vision correction surgery may include lens implantation.

As another example, in the operation S3400 of predicting whether the subject needs custom vision correction surgery, a second vision correction surgery may be output based on a first vision correction surgery determined in the operation S3500 of suggesting vision correction surgery corresponding to the subject. Here, the first vision correction surgery may be a surgery determined without consideration of the custom vision correction surgery necessity, and the second vision correction surgery may be a surgery determined in consideration of the custom vision correction surgery necessity.

As yet another example, whether to perform the operation S3400 of predicting whether the subject needs custom vision correction surgery may be determined based on a type of the first vision correction surgery determined in the operation S3500 of suggesting the vision correction surgery corresponding to the subject. For example, when the first vision correction surgery is a first type of vision correction surgery, the custom vision correction surgery necessity prediction model may not be executed, and when the first vision correction surgery is a second type of vision correction surgery, the custom vision correction surgery necessity prediction model may be executed.

The first type and the second type may be distinguished according to whether a cornea is cut using a laser. For example, the first type may be a non-laser vision correction surgery such as lens implantation, and the second type may be a laser vision correction surgery such as LASIK, LASEK, SMILE.

The first type and the second type may be distinguished according to whether a custom surgery is possible. For example, the first type may be a vision correction surgery in which a custom surgery is not possible, and the second type may be vision correction surgery in which custom surgery is possible. Here, a predetermined criterion may exist as to whether the vision correction surgery is a surgery in which a custom surgery is possible. However, the criterion may vary according to technological advancement, hospitals', surgical devices', and doctors' circumstances and determinations, and the like. For example, when a custom SMILE surgery is not possible, the first type may include SMILE and lens implantation, and the second type may include LASIK and LASEK. On the other hand, when the custom SMILE surgery is possible, the first type may include lens implantation, and the second type may include LASIK, LASEK, and SMILE.

Figure 38:
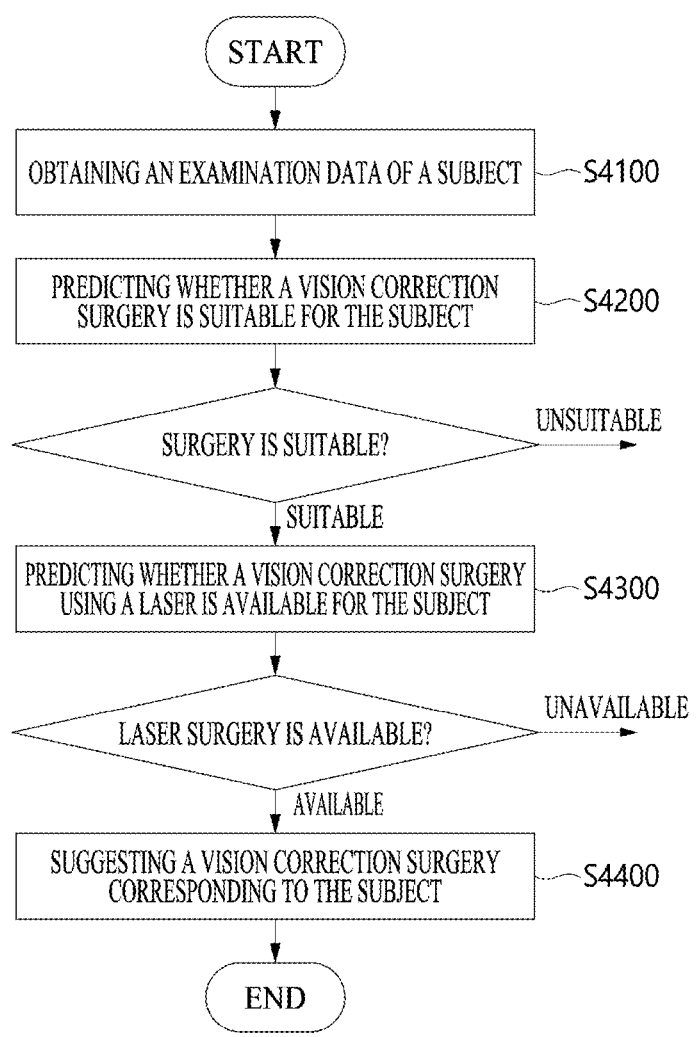
FIG. 38 is a diagram illustrating a fourth example of the method of recommending the vision correction surgery according to an embodiment.

FIG. 38 is a diagram illustrating a fourth example of the method of recommending the vision correction surgery according to an embodiment.

Referring to FIG. 38, the method of recommending the vision correction surgery according to an embodiment may include an operation S4100 of obtaining examination data of a subject, an operation S4200 of predicting whether a vision correction surgery is suitable for the subject, an operation S4300 of predicting whether a vision correction surgery using a laser is available for the subject, and an operation S4400 of suggesting a vision correction surgery corresponding to the subject.

Since the operation S4100 of obtaining the examination data of the subject, the operation S4200 of predicting whether the vision correction surgery is suitable for the subject, and the operation S4300 of predicting whether the vision correction surgery using the laser is available for the subject of FIG. 38 are the same as those of FIG. 35, descriptions thereof will be omitted.

The operation S4400 of suggesting the vision correction surgery corresponding to the subject may include suggesting the vision correction surgery corresponding to the subject by inputting third group data obtained from the examination data of the subject to a third prediction model.

Whether to perform the operation S4400 may depend on whether the vision correction surgery using the laser is available for the subject. For example, the operation S4400 may be performed when the vision correction surgery using the laser is available for the subject. In the operation S4400, a vision correction surgery may be suggested based on a conical shape factor prediction value of the subject after a standard vision correction surgery and a corneal shape factor prediction value of the subject after a custom vision correction surgery.

The third prediction model may be a model in which a custom vision correction surgery necessity prediction model and a vision correction surgery suggestion model are merged with each other. The third prediction model may be trained based on at least one selected from the group of pieces of examination data of a plurality of patients who have undergone vision correction surgeries, vision correction surgeries corresponding to the plurality of patients, and visual abilities of the plurality of patients after the vision correction surgeries. The third prediction model may output information about at least one of a custom vision correction surgery necessity or a vision correction surgery based on the third group data. For example, an output of the third prediction model may include at least one of the custom vision correction surgery necessity or the vision correction surgery.

Figure 39:
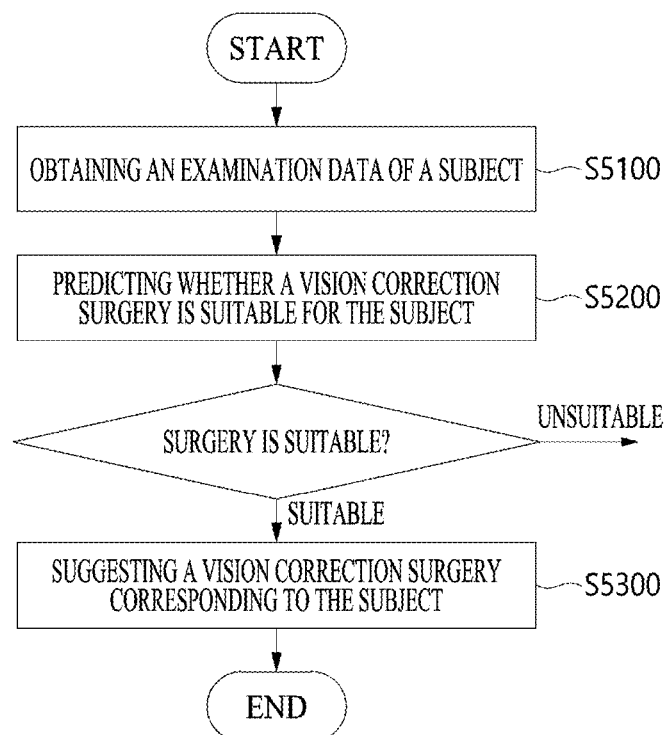
FIG. 39 is a diagram illustrating a fifth example of the method of recommending the vision correction surgery according to an embodiment.

FIG. 39 is a diagram illustrating a fifth example of the method of recommending the vision correction surgery according to an embodiment.

Referring to FIG. 39, the method of recommending the vision correction surgery according to an embodiment may include an operation S5100 of obtaining examination data of a subject, an operation S5200 of predicting whether a vision correction surgery is suitable for the subject, and an operation S5300 of suggesting a vision correction surgery corresponding to the subject.

Since the operation S5100 of obtaining the examination data of the subject and the operation S5200 of predicting whether the vision correction surgery is suitable for the subject illustrated in FIG. 39 are to the same as those of FIG. 35, descriptions thereof will be omitted.

The operation S5300 of suggesting the vision correction surgery corresponding to the subject may include suggesting the vision correction surgery corresponding to the subject by inputting second group data obtained from the examination data of the subject to a second prediction model.

Whether to perform the operation S5300 may depend on whether the vision correction surgery is suitable for the subject. For example, the operation S5300 may be performed when the vision correction surgery is suitable for the subject. In the operation S5300, a vision correction surgery may be suggested based on a corneal shape factor prediction value of the subject after a standard vision correction surgery and a corneal shape factor prediction value of the subject after a custom vision correction surgery.

The second prediction model may be a model in which a laser surgery availability prediction model, a custom vision correction surgery necessity prediction model, and a vision correction surgery suggestion model are merged. The second prediction model may be trained based on at least one selected from the group of pieces of examination data of a plurality of patients who have undergone vision correction surgeries, vision correction surgeries corresponding to the plurality of patients, and visual abilities of the plurality of patients after vision correction surgeries. The second prediction model may output information about at least one selected from the group of a laser surgery availability, a custom vision correction surgery necessity, and a vision correction surgery based on the second group data. For example, an output of the second prediction model may include at least one selected from the group of the laser surgery availability, the custom vision correction surgery necessity, and the vision correction surgery.

Figure 40:
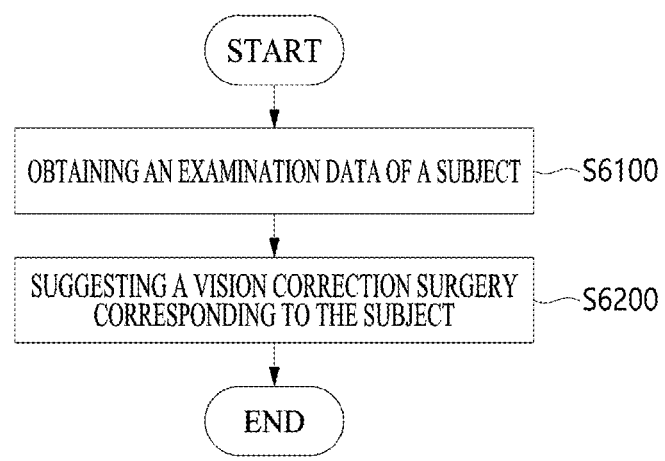
FIG. 40 is a diagram illustrating a sixth example of the method of recommending the vision correction surgery according to an embodiment.

FIG. 40 is a diagram illustrating a sixth example of the method of recommending the vision correction surgery according to an embodiment.

Referring to FIG. 40, the method of recommending the vision correction surgery according to an embodiment may include an operation S6100 of obtaining examination data of a subject and an operation S6200 of suggesting a vision correction surgery corresponding to the subject.

Since the operation S6100 of obtaining the examination data of the subject of FIG. 40 is to the same as that of FIG. 35, a description thereof will be omitted.

The operation S6200 of suggesting the vision correction surgery corresponding to the subject may include suggesting the vision correction surgery corresponding to the subject by inputting group data obtained from the examination data of the subject to a prediction model. In the operation S6200, a vision correction surgery may be suggested based on a corneal shape factor prediction value of the subject after a standard vision correction surgery and a corneal shape factor prediction value of the subject after a custom vision correction surgery.

The prediction model may be a model in which a surgery suitability prediction model, a laser surgery availability prediction model, a custom vision correction surgery necessity prediction model, and a vision correction surgery suggestion model are merged. The prediction model may be trained based on at least one selected from the group of pieces of examination data of a plurality of patients who have undergone vision correction surgeries, vision correction surgeries corresponding to the plurality of patients, and visual abilities of the plurality of patients after vision correction surgeries. The prediction model may output information about at least one selected from the group of a surgery suitability, a laser surgery availability, a custom vision correction surgery necessity, and a vision correction surgery based on input data. For example, an output of the prediction model may include at least one selected from the group of the surgery suitability, the laser surgery availability, the custom vision correction surgery necessity, and the vision correction surgery.

The combination and/or merging of the methods for recommending the vision correction surgery and the vision correction surgery related models is only exemplary and, in addition, the methods for recommending the vision correction surgery may be implemented or the vision correction surgery related models may be combined and/or merged in various ways.

Hereinafter, examples of a method of providing vision correction surgery visualization information will be described.

The method of providing the vision correction surgery visualization information may be implemented using one or more vision correction surgery related models. When the method is implemented using a plurality of vision correction surgery related models, whether to execute at least one vision correction surgery related model may depend on a prediction result of at least another vision correction surgery related model. For example, whether to execute a second vision correction surgery related model may depend on a prediction result of a first vision correction surgery related model.

The method of providing the vision correction surgery visualization information may include a method of providing an expected visual ability image, a method of providing a corneal topography image, and a method of providing a prediction result calculation cause.

The method of providing the expected visual ability image may be implemented using an expected visual ability image generation model. The method of providing the corneal topography image may be implemented using a corneal topography image prediction model. The method of providing the prediction result calculation cause may be implemented using a prediction result calculation cause analysis model.

Operations of the method of providing the vision correction surgery visualization information which will be described below may be performed by a prediction device.

Figure 41:
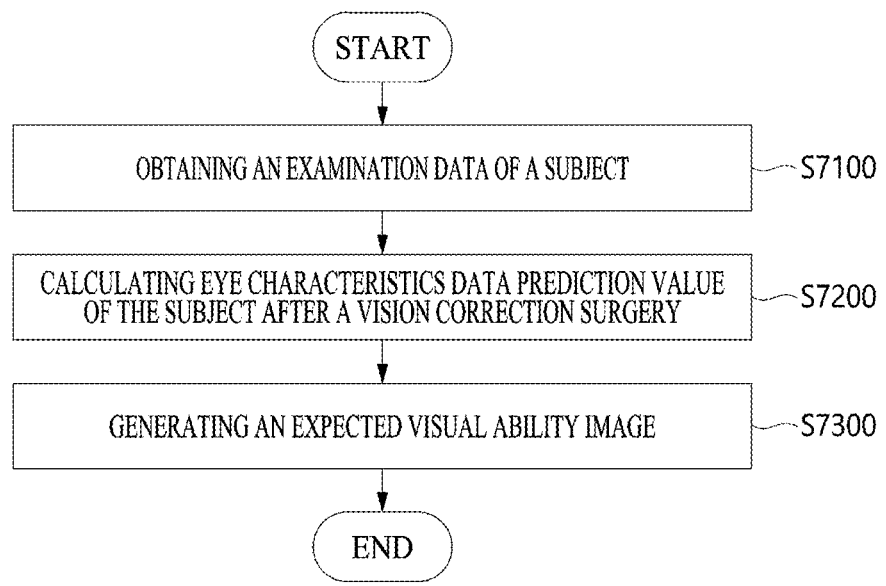
FIG. 41 is a diagram illustrating a first example of a method of providing vision correction surgery visualization information according to an embodiment.

FIG. 41 is a diagram illustrating a first example of a method of providing vision correction surgery visualization information according to an embodiment.

Referring to FIG. 41, the method of providing the vision correction surgery visualization information according to an embodiment may include an operation S7100 of obtaining examination data of a subject, an operation S7200 of calculating a prediction value of eye characteristic data of the subject after a vision correction surgery, and an operation S7300 of generating an expected visual ability image. Further, although not illustrated, the method of providing the vision correction surgery visualization information according to an embodiment may further include outputting the expected visual ability image.

The operation S7100 of obtaining the examination data of the subject may include obtaining, by a computing device, the examination data including interview data and a measurement of eye characteristic data.

The operation S7200 of calculating a prediction value of eye characteristic data of the subject after a vision correction surgery may include calculating a prediction value of eye characteristic data including at least one of a predicted visual ability value of the subject or a corneal shape factor prediction value after a vision correction surgery by inputting first group data obtained from the examination data of the subject to a first prediction model.

The first prediction model may be trained based on at least one selected from the group of measurements of pieces of eye characteristic data before surgery of a plurality of patients who have undergone vision correction surgeries, surgery parameters of the vision correction surgeries performed on the plurality of patients, and measurements of the pieces of the eye characteristic data after surgery of the plurality of patients. The first prediction model may include at least one of a visual ability prediction model or a corneal shape factor prediction model. Alternatively, the first prediction model may be a model in which a visual ability prediction model and a corneal shape factor prediction model are merged. The first prediction model may calculate a prediction value of eye characteristic data of the subject after a vision correction surgery based on the first group data.

The operation S7300 of generating the expected visual ability image may include generating the expected visual ability image based on the prediction value of the eye characteristic data.

Figure 42:
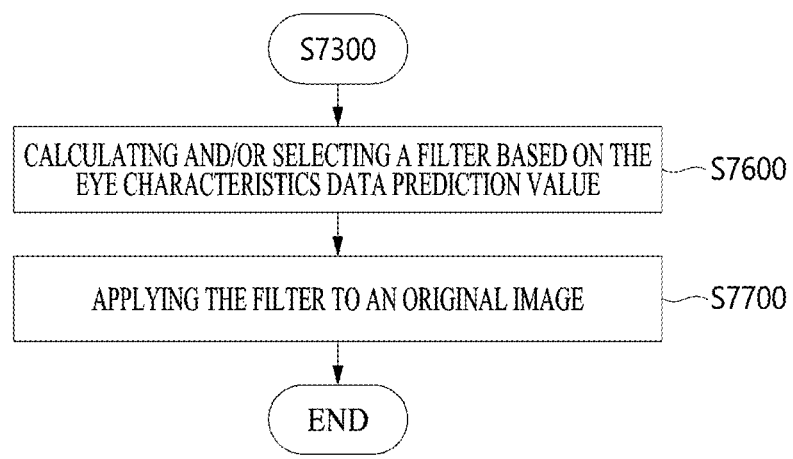
FIG. 42 is a diagram illustrating a second example of the method of providing the vision correction surgery visualization information according to an embodiment.

FIG. 42 is a diagram illustrating a second example of the method of providing the vision correction surgery visualization information according to an embodiment Referring to FIG. 42, the method of providing the vision correction surgery visualization information according to an embodiment may further include an operation S7600 of calculating and/or selecting a filter based on the prediction value of the eye characteristic data and an operation S7700 of applying the filter to an original image.

An operation S7600 of calculating and/or selecting the filter based on the prediction value of the eye characteristic data may be performed by the first sub-model M171 of FIG. 11.

The operation S7700 of applying the filter to the original image may include applying the filter to the original image to generate the expected visual ability image. The operation S7700 may be performed by the second sub-model M172 of FIG. 11.

Figure 43:
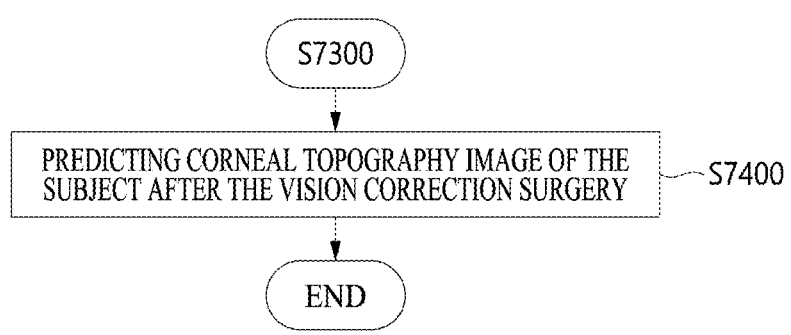
FIG. 43 is a diagram illustrating a third example of the method of providing the vision correction surgery visualization information according to an embodiment.

FIG. 43 is a diagram illustrating a third example of the method of providing the vision correction surgery visualization information according to an embodiment.

Referring to FIG. 43, the method of providing the vision correction surgery visualization information according to an embodiment may further include an operation S7400 of predicting a corneal topography image of the subject after a vision correction surgery.

The operation S7400 of predicting the corneal topography image of the subject after the vision correction surgery may include predicting the corneal topography image of the subject after the vision correction surgery by inputting second group data obtained from the examination data of the subject to a second prediction model.

The second prediction model may be trained based on at least one selected from the group of corneal topography images before surgeries of a plurality of patients who have undergone vision correction surgeries, surgery parameters of the vision correction surgeries performed on the plurality of patients, and corneal topography images after the surgeries of the plurality of patients. The second prediction model may be a corneal topography image prediction model. The second prediction model may predict a corneal topography image of the subject after a vision correction surgery based on the second group data.

Figure 44:
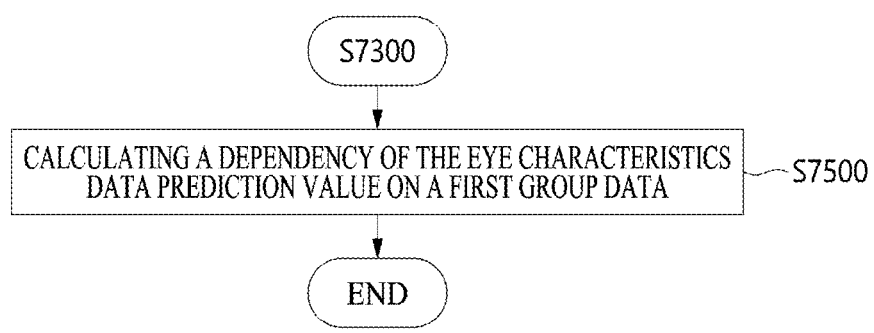
FIG. 44 is a diagram illustrating a fourth example of the method of providing the vision correction surgery visualization information according to an embodiment.

FIG. 44 is a diagram illustrating a fourth example of the method of providing the vision correction surgery visualization information according to an embodiment.

Referring to FIG. 44, the method of providing the vision correction surgery visualization information according to an embodiment may further include an operation S7500 of calculating a dependency of a prediction value of eye characteristic data on first group data. Further, although not illustrated, the method of providing the vision correction surgery visualization information according to an embodiment may further include outputting a dependency coefficient.

The outputting of the dependency coefficient may include outputting a dependency coefficient, which is greater than a predetermined value, among dependency coefficients or outputting a predetermined number of dependency coefficients.

The methods according to embodiments may be implemented in the form of program instructions that can be executed through various computer units and recorded in computer readable media. The computer readable media may include a program instruction, a data file, a data structure, or combinations thereof. The program instruction recorded in the computer readable media may be specially designed and prepared for embodiments or may be an possible well-known instruction for those skilled in the field of computer software. Examples of the computer readable media include magnetic media such as a hard disk, a floppy disk, and a magnetic tape, optical media such as a compact disc read-only memory (CD-ROM) and a digital video disc (DVD), magneto-optical media such as a floptical disk, and a hardware device, such as a ROM, a RAM, or a flash memory, that is specially made to store and execute the program instruction. Examples of the program instruction may include a machine code generated by a compiler and a high-level language code that can be executed in a computer using an interpreter. Such a hardware device may be configured as at least one software module in order to perform operations of an embodiments and vice versa.

In the above, the configurations and features of the present invention have been described based on an embodiments, but the present invention is not limited thereto, and it will be apparent to those skilled in the art that various changes or modifications can be made within the spirit and scope of the present invention. Therefore, it is revealed that such changes or modifications fall within the scope of the appended claims.

MODE OF INVENTION

As described above, in the technical solutions of the present invention, related matters have been described.

The invention claimed is:

1. A method performed by a computing device, the method comprising:
 obtaining an examination data of a subject, wherein the examination data includes a demographic data and a measurement of an eye characteristics data, the measurement of the eye characteristics data includes one or more measurement values representing corneal shape of the subject before a vision correction surgery, and the measurement values include at least one selected from the group of an index of height decentration (IHD) before a vision correction surgery, an index of surface variance (ISV) before a vision correction surgery, and an index of vertical asymmetry (IVA) before a vision correction surgery;
 calculating one or more first prediction values and one or more second prediction values by inputting a first group data to a first prediction model,
 wherein the first group data is acquired from the examination data of the subject,
 wherein the first prediction values represent a predicted corneal shape of the subject after a laser vision correction surgery with predetermined surgery parameters and the second prediction values represent a predicted corneal shape of the subject after a laser vision correction surgery with customized surgery parameters,
 wherein the first prediction values include at least one selected from the group of a predicted index of height decentration (IHD) after the laser vision correction surgery with predetermined surgery parameters, a predicted index of surface variance (ISV) after the laser vision correction surgery with predetermined surgery parameters, and a predicted index of vertical asymmetry (IVA) after the laser vision correction surgery with predetermined surgery parameters, and wherein the second prediction values include at least one selected from the group of a predicted IHD after the laser vision correction surgery with customized surgery parameters, a predicted ISV after the laser vision correction surgery with customized surgery parameters, and a predicted IVA after the laser vision correction surgery with customized surgery parameters;

outputting the measurement values, the first prediction values, and the second prediction values for determining whether the laser vision correction surgery with customized surgery parameters is necessary for the subject based on the measurement values, the first prediction values, and the second prediction values; and suggesting a type of a vision correction surgery corresponding to the subject by inputting a second group data to a second prediction model, wherein the suggested type is LASIK, LASEK, or SMILE, and wherein the second group data is acquired from the examination data of the subject, wherein the second prediction model is trained based on at least one selected from the group of the examination data of a plurality of patients undergoing a vision correction surgery, types of vision correction surgeries corresponding to the plurality of patients and visual abilities of the plurality of patients after the vision correction surgeries, and wherein a recommended vision correction surgery for the subject is determined by combining results obtained by the first and the second prediction models whereby the recommended vision correction surgery for the subject is one of LASIK with predetermined surgery parameters, LASEK with predetermined surgery parameters, SMILE with predetermined surgery parameters, LASIK with customized surgery parameters, LASEK with customized surgery parameters, and SMILE with customized surgery parameters.

2. The method of claim 1, wherein the suggesting comprises suggesting the type based on one or more predicted visual ability values of the subject after one or more vision correction surgeries.

3. The method of claim 2, wherein the suggesting comprises suggesting the type by calculating the one or more predicted visual ability values of the subject after the one or more vision correction surgeries, each of the predicted visual ability values corresponding to each of the vision correction surgeries.

4. The method of claim 2, wherein the suggesting comprises suggesting the type by calculating a plurality of predicted visual ability values corresponding to a plurality of different time points.

5. The method of claim 1, wherein the method further comprises determining whether the laser vision correction surgery with customized surgery parameters is necessary for the subject based on the measurement values, the first prediction values, and the second prediction values.

6. The method of claim 1, further comprising:

predicting whether a vision correction surgery is suitable for the subject by inputting a third group data to a surgery suitability prediction model, the third group data being acquired from the examination data of the subject; and when a vision correction surgery is suitable for the subject, predicting whether the laser vision correction surgery is available for the subject by inputting a fourth group data to a laser surgery availability prediction model, the fourth group data being acquired from the examination data of the subject.

7. The method of claim 1, wherein when the second prediction model is trained by considering preferences of the plurality of patients for a vision correction surgery, the second group data includes a preference of the subject for a vision correction surgery.

8. The method of claim 1, wherein at least one of the first prediction model or the second prediction model includes a plurality of sub-models, and calculates a result based on results of the plurality of sub-models.

9. The method of claim 1, wherein at least one of the first group data or the second group data includes at least a portion of the examination data of the subject as it is, or includes a new type of data calculated from at least a portion of the examination data of the subject.

10. The method of claim 1, wherein the examination data further includes genetic information.

11. A non-transitory computer-readable medium readable by a computing device and recording a program for executing the method of claim 1 on the computing device.

* * * * *